United States Patent
Yoshimizu et al.

(10) Patent No.: US 8,553,216 B2
(45) Date of Patent: Oct. 8, 2013

(54) DEFECT INSPECTION DEVICE USING CATADIOPTRIC OBJECTIVE LENS

(75) Inventors: Keiko Yoshimizu, Yokohama (JP); Yasuhiro Yoshitake, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 373 days.

(21) Appl. No.: 12/747,949

(22) PCT Filed: Dec. 19, 2008

(86) PCT No.: PCT/JP2008/073215
§ 371 (c)(1),
(2), (4) Date: Dec. 21, 2010

(87) PCT Pub. No.: WO2009/118966
PCT Pub. Date: Oct. 1, 2009

(65) Prior Publication Data
US 2012/0281207 A1    Nov. 8, 2012

(30) Foreign Application Priority Data

Mar. 24, 2008 (JP) ................................. 2008-074847

(51) Int. Cl.
*G01N 21/00* (2006.01)
(52) U.S. Cl.
USPC ....................................... 356/237.5
(58) Field of Classification Search
None
See application file for complete search history.

(56) References Cited

U.S. PATENT DOCUMENTS

| | | | |
|---|---|---|---|
| 5,617,203 A * | 4/1997 | Kobayashi et al. | 356/237.5 |
| 5,999,310 A * | 12/1999 | Shafer et al. | 359/351 |
| 6,064,517 A * | 5/2000 | Chuang et al. | 359/364 |
| 6,560,039 B1 | 5/2003 | Webb et al. | |
| 6,954,266 B2 | 10/2005 | Tomie | |
| 7,095,508 B2 * | 8/2006 | Hill | 356/512 |
| 7,351,980 B2 * | 4/2008 | Lange | 250/372 |
| 7,433,033 B2 * | 10/2008 | Bleeker et al. | 356/237.2 |
| 7,957,066 B2 * | 6/2011 | Armstrong et al. | 359/618 |

(Continued)

FOREIGN PATENT DOCUMENTS

| | | | |
|---|---|---|---|
| JP | 08021800 A | * | 1/1996 |
| JP | 10-177139 | | 6/1998 |
| JP | 2000-260376 | | 9/2000 |
| JP | 2003-114200 | | 4/2003 |

(Continued)

OTHER PUBLICATIONS

Yasuhiro Yoshitake et al., Broadband alignment scheme for a stepper system using combinations of diffractive and refractive lenses, Applied Optics, Dec. 1, 1994, pp. 7971-7979, vol. 33, No. 34.

(Continued)

*Primary Examiner* — Gordon Stock, Jr.
(74) *Attorney, Agent, or Firm* — Antonelli, Terry, Stout & Kraus, LLP.

(57) ABSTRACT

A defect inspection device comprises an inspection optical system including a light source, a half mirror for reflecting illumination light emitted from the light source, a catadioptric objective lens for collecting reflected light from the sample by illumination light reflected by the half mirror, an imaging lens for focusing the reflected light transmitted through the catadioptric objective lens, a relay lens having a blocking member provided at a position at which specularly reflected light from the sample is focused by the imaging lens, and a detector for detecting specularly reflected light not blocked by the blocking member; and a computation processing unit for detecting defects of the sample on the basis of the signals detected by the detector.

21 Claims, 24 Drawing Sheets

(56) References Cited

U.S. PATENT DOCUMENTS

| | | | |
|---|---|---|---|
| 2002/0085271 A1 | 7/2002 | Shafer et al. | |
| 2007/0019856 A1* | 1/2007 | Furman et al. | 382/141 |
| 2007/0153265 A1* | 7/2007 | Vaez-Iravani et al. | 356/237.5 |
| 2007/0195315 A1* | 8/2007 | Goldberg et al. | 356/237.2 |
| 2008/0225282 A1* | 9/2008 | Chuang et al. | 356/237.4 |
| 2008/0297783 A1* | 12/2008 | Urano et al. | 356/237.5 |
| 2009/0080065 A1* | 3/2009 | Shafer et al. | 359/354 |
| 2011/0085179 A1* | 4/2011 | Mann et al. | 356/614 |
| 2011/0242528 A1* | 10/2011 | Hwang et al. | 356/237.2 |
| 2011/0292390 A1* | 12/2011 | Shibata et al. | 356/369 |
| 2012/0242970 A1* | 9/2012 | Smilde et al. | 355/77 |

FOREIGN PATENT DOCUMENTS

| | | |
|---|---|---|
| JP | 2004-193269 | 7/2004 |
| JP | 2005-241290 | 9/2005 |
| JP | 2008-014823 | 1/2008 |
| JP | 2008-039444 | 2/2008 |

OTHER PUBLICATIONS

Byoung-Ho Lee et al., Polarization Control for Enhanced Defect Detection on Advanced Memory Devices, Proc. of SPIE, 61521Q-1-61521Q-6, vol. 6152.

* cited by examiner

DEFECT INSPECTION DEVICE USING CATADIOPTRIC OBJECTIVE LENS

INCORPORATION BY REFERENCE

The present application claims priority from Japanese application JP-2008-074847 filed on Mar. 24, 2008, the content of which is hereby incorporated by reference into this application.

TECHNICAL FIELD

This invention relates to a defect inspection device for inspecting defects on a wafer surface.

BACKGROUND ART

Foreign matters on a semiconductor substrate (wafer), if any, may result in defects of wiring such as inferior insulation and short-circuit in a semiconductor manufacturing process. When a semiconductor device is miniaturized and fine foreign matters exist inside the semiconductor substrate, the foreign matters may result in an insulation defect of a capacitor and breakdown of a gate oxide film. These foreign matters are generated owing to diversified causes such as those which occur from movable portions of a conveyor apparatus and from the human body, those which are generated due to the reaction inside a processing apparatus using process gases and those which are mixed in chemicals and materials, and are mixed under diversified conditions. A defect inspection device is known as a device for inspecting these foreign matters and includes an illumination optical system, a detection optical system and an image processing system.

The paper "Broadband alignment scheme for a stepper system using combinations of diffractive and refractive lenses", Applied Optics, v. 33, No. 34, pp 7971-7979(1994) describes the use of a plurality of wavelengths for reducing the change of light power resulting from the change of a film thickness in the illumination optical system. To correct chromatic aberration necessary for acquiring high resolution images using a plurality of wavelengths, U.S. Pat. No. 6,560,039 B1 teaches that Schwarzschild catoptrics objective lenses (catoptrics objective lenses) are more effective than dioptrics objective lenses.

"Polarization Control for Enhanced Defect Detection on Advanced Memory Devices", Proceeding of SPIE Vol. #6152 (2006) describes a method for accomplishing defect detection with high sensitivity by radiating illumination light to a wiring short-circuit unit at the bottom of a semiconductor substrate by illumination. Because a Schwarzschild catoptric objective lens has a reflecting film or a reflecting surface at a lens center, however, vertical illumination cannot be made by using the Schwarzschild objective lens. Therefore, U.S. Pat. No. 6,954,266 B2 discloses a method for vertically radiating rays of light from a light source onto a sample by arranging a mirror between a Schwarzschild objective lens and a sample surface or a mirror between a Schwarzschild objective lens group and a detector.

JP-A-10-177139 describes an illumination and detection method for detecting foreign matters adhering to a sample through a catadioptric objective lens by radiating light from a light source onto the sample by inclined illumination or vertical illumination.

DISCLOSURE OF THE INVENTION

Correction of chromatic aberration is necessary for using a plurality of wavelengths suitable for reducing the change of light power resulting from the change of a film thickness of a semiconductor substrate and the like U.S. Pat. No. 6,560,039 B1 describes that a Schwarzschild catoptrics objective lens is effective for executing the correction of chromatic aberration. However, because the Schwarzschild catoptrics objective lens has a reflecting film or a reflecting surface at a lens center, it involves the problem that vertical illumination effective for detecting the defects cannot be made by causing the illumination light to reach a wiring short-circuit unit.

U.S. Pat. No. 6,954,426 B2 describes a construction capable of vertical illumination by interposing a mirror between a Schwarzschild catoptrics objective lens and a sample surface but NA cannot be increased because a space must be secured sufficiently between the Schwarzschild catoptrics objective lens and the sample surface. U.S. Pat. No. 6,954,426 B2 proposes also a construction capable of vertical illumination by arranging a mirror between a Schwarzschild catoptrics objective lens and a detector and forming a hole in the Schwarzschild catoptrics objective lens. However, there remains the problem that an S/N ratio is low because specularly reflected light from a defect transmitted through the Schwarzschild catoptric objective lens is not focused but results in a flare component on the detection surface.

The catadioptric objective lens described in JP-A-10-177139 has a construction capable of vertical illumination but is not free from the problem of the low S/N because the specularly reflected light transmitted through the center of the catadioptric objective lens is not focused but results in the flare component on the detection surface.

The explanation of typical inventions among those disclosed in this application is briefly as follows.

(1) A defect inspection device having an inspection optical system that includes a light source, a half mirror for reflecting illumination light emitted from the light source, a catadioptric objective lens for collecting reflected light from a sample by the illumination light reflected from the half mirror, an imaging lens for focusing the reflected light transmitted through the catadioptric objective lens, a relay lens having a blocking member provided at a position at which specularly reflected light from the sample is focused by the imaging lens, and a detector for detecting specularly reflected light not blocked by the blocking member; and a computation processing unit for detecting defects of the sample on the basis of the signals detected by the detector.

(2) A defect inspection device described in item (1), wherein the catadioptric objective lens has a dioptric lens for refracting first reflected light from the sample and a reflecting member having a first reflecting surface for reflecting a part of the first reflected light, a region for reflecting second reflected light reflected by the reflecting surface and a region for transmitting specularly reflected light by the sample.

The invention can provide a defect inspection device that can accomplish high NA and high SN by vertical illumination by using a catadioptric objective lens.

Other objects, features and advantages of the invention will become obvious from the following description of embodiments thereof taken in conjunction with the accompanying drawings.

BEST MODE FOR CARRYING OUT THE INVENTION

An inspection optical system according to embodiments of the invention will be explained with reference to the drawings.

Embodiment 1

A first embodiment will be explained with reference to FIG. 1. FIG. 1 relates to an inspection optical system for inspecting a to-be-inspected object (wafer) 1.

The inspection optical system includes an illumination light source 211 for emitting illumination light to the wafer 1, a half mirror 205a for turning back the illumination light illuminated by the illumination light source 211 and emitting the illumination light to the wafer 1, a catadioptric objective lens having a convex reflecting member 207, a convex reflecting surface 206 and a dioptric objective lens group 208, an imaging lens 204 for focusing the reflected light from the wafer 1 transmitted through the catadioptric objective lens, a blocking member 213a arranged at a position at which the specularly reflected light from the wafer 1 contained in the reflected light is focused by the imaging lens 204, a first relay lens 203 having the blocking member 213a, a second relay lens 202 for transmitting specularly reflected light not blocked by the blocking member 213a of the first relay lens 203, and a detector 201a for detecting the reflected light transmitted through the second relay lens 202. Here, the convex reflecting member 207, the concave reflecting surface 206a and the dioptric lens group 208 constitute the catadioptric lens group.

The illumination light emitted from the illumination light source 211 shown in FIG. 1 is turned back by the half mirror 205a, is radiated vertically to the surface of the wafer 1 and creates the reflected light. Scattered light contained in the reflected light is reflected by the concave reflecting surface 206 and is again reflected by the convex reflecting member 207. The specularly reflected light component contained in the reflected light is transmitted through the light transmission region formed at the center of the convex reflecting member 207. After an image of the scattered light is once formed by the imaging lens 204, the scatter light is transmitted through the relay lenses 203 and 202 and is again focused and detected by the detector 201a. The specularly reflected light is focused by the imaging lens 204 and is blocked by the blocking member 213a. As a result, because only the scattered light is detected by the detector 201a, the flare component is removed and detection with reduced noise becomes possible to provide a high signal-to-noise ratio SN. Incidentally, a beam splitter can be used in place of the half mirror 205a.

FIGS. 5A and 5B show an example of the surface of the wafer 1. The wafer surface 1 has a line-and-space structure 501 or a dot pattern structure 502. Vertical illumination is necessary for detecting the defects when wiring short-circuit units 503 and 504 exist at the bottom of the line-and-space 501 or the bottom of the dot pattern 502 as shown in the drawings.

FIG. 4 shows an example of the illumination light source 211. The illumination light source 211 includes a plurality of laser light sources 211a, 211b, 211c and 211d having mutually different wavelengths and dichroic mirrors 212a, 212b and 212c for reflecting or transmitting only a specific wavelength, and emits illumination light 214 synthesized by a plurality of laser beams having mutually different wavelengths. Incidentally, the wavelength of the laser light sources is not particularly limited to the four wavelengths but may have at least two wavelengths, and the dichroic mirrors may be added with the number of the wavelengths. The third harmonics SHG of a high output YAG laser having a wavelength 355 nm can be used conveniently as the illumination light source 211 for the purpose of branching but 355 nm is not always indispensable. The illumination light source 211 need not always be YAGSHG, either. In other words, the illumination light source 211 may be an Ar laser, a nitrogen laser, a He—Cd laser, excimer laser, or the like.

FIGS. 6A and 6B show an example of the convex reflecting member 207. The convex reflecting member 207a shown in FIG. 6A has a center hole 237a, through which light can be transmitted, at the center of the reflecting surface 227a and can emit the illumination light from the turn-back mirror 205a shown in FIG. 1 without reflection. Therefore, it can accomplish vertical illumination.

FIG. 6B shows a convex reflecting member 207b as another form of the convex reflecting member 207. The convex reflecting member 207b may be constituted by a convex dioptric lens. In FIG. 6B, a reflecting film is applied to the lens as the convex reflecting member 207b to form the reflecting surface 227b. In this case, too, vertical illumination can be accomplished by forming a light transmission region 237b without applying the reflecting film to the center of the convex dioptric member 207b. Incidentally, the region of the reflecting film is not limited to the region shown in FIG. 6B but can be decided arbitrarily. A reflecting film is applied to the dioptric lens group 208 constituting the catadioptric objective lens and the resulting lens can be used also as the convex reflecting member 207 in place of the convex reflecting member 207.

FIG. 7 shows an example of each of the first relay lens 203 and the blocking member 213a. A blocking member 213a through which light cannot be transmitted is formed by applying a blocking film to the center of the first relay lens 203. Because the blocking member 213a can block the specularly reflected light from the wafer 1, the noise that has so far been detected as the flare component can be reduced.

FIGS. 8A and 8B are explanatory views about optical paths of the specularly reflected light and the scattered light from the surface of the wafer 1. The specularly reflected light shown in FIG. 8A is transmitted through the imaging lens 204 but is blocked by the blocking member 213 provided to the first relay lens 203. Therefore, it is not detected by the detector 201a. On the other hand, because the scattered light shown in FIG. 8B can be transmitted through the imaging lens 204 and the image is formed, it can be then transmitted through the first relay lens 203. Therefore, it is not blocked by the blocking member 213 and is detected by the detector 201a.

Embodiment 2

A second embodiment will be explained with referenced to FIG. 2. Here, only the difference from the first embodiment will be explained. The inspection optical system shown in FIG. 2 has the construction in which a spatial filter 209 having the blocking member 213b is arranged at a position at which the specularly reflected light from the wafer 1 is focused by the imaging lens 204. Because the specularly reflected light from the wafer 1 is blocked by the blocking member 213b provided to the spatial filter 209, the detector 201b detects only the scattered light from the wafer 1 and high S/N by the reduction of the flare component can be accomplished in the same way as in the first embodiment.

FIG. 9 shows an example of sectional and top views of a first relay lens 203, a spatial filter 209 and a blocking member 213b in the inspection optical system according to the second embodiment. However, the top view of the first relay lens 203 is shown deviated from that of the spatial filter 209 for ease of explanation.

Because the spatial filter 209 having the blocking member 213b is arranged at a position at which the specularly reflected light is focused by the imaging lens 204, it is possible to form a region through which light cannot be transmitted and to block the specularly reflected light radiated to the wafer surface 1. Therefore, the noise detected as the flare component can be reduced.

FIGS. 10A and 10B are explanatory views about optical paths of the specularly reflected light and the scattered light from the wafer surface 1 in the second embodiment. The specularly reflected light shown in FIG. 10A is transmitted through the imaging lens 204 and is blocked by the blocking surface 213b provided to the center of the spatial filter 209. Therefore, it is not detected by the detector 201b. On the other hand, the scattered light shown in FIG. 10B is once focused by the imaging lens 204, is again focused without being blocked by the blocking member 213b and is then detected by the detector 201b.

Embodiment 3

A third embodiment will be explained with referenced to FIG. 3. Here, only the differences from the first and second embodiments will be explained. In the inspection optical system shown in FIG. 3, a spatial filter 209 having a circular cylindrical turn-back mirror 213c is arranged at a position at which the specularly reflected light of the wafer 1 is focused and an illumination light source 211 is arranged in such a fashion that the rays of light can be turned back by this turn-back mirror 213c. This turn-back mirror 213c plays the role of the blocking member for blocking the specularly reflected light and the role of the turn-back member for turning back the illumination light and achieving vertical illumination.

FIG. 11 shows an example of sectional and top views of a first relay lens 203, a spatial filter 209 and a turn-back mirror 213c as a blocking member in the third embodiment. However, the top view of the first relay lens 203 is shown deviated from that of the spatial filter 209 for ease of explanation.

Because the spatial filter 209 having the blocking member 213b is arranged at a position at which the specularly reflected light from the wafer 1 is focused by the imaging lens 204, it is possible to form a region through which light cannot be transmitted and to block the specularly reflected light radiated to the wafer surface 1. Therefore, the noise detected as the flare component can be reduced and a high SN can be achieved. Because the blocking member can be used also as the turn-back member, the size of the inspection optical system can be reduced and the number of production steps in the manufacturing process can be decreased. Thus, a lower cost of production can be accomplished.

FIGS. 12A and 12B are explanatory views about optical paths of the specularly reflected light and the scattered light from the wafer surface 1 in the third embodiment. The specularly reflected light shown in FIG. 12A is transmitted through the imaging lens 204 and is blocked by a circular cylindrical turn-back mirror 213c provided to the center of the spatial filter 209. Therefore, it is not detected by the detector 201c. On the other hand, the scattered light shown in FIG. 12B is transmitted through the imaging lens 204, is focused by the imaging lens 204 and is then detected by the detector 201c without being blocked by the turn-back mirror 213c.

Next, FIGS. 13A to 13C show the optical path of the specularly reflected light in each of the embodiments. Referring to FIG. 13A, the specularly reflected light from the wiring short-circuit unit 503, 504 is transmitted through the catadioptric objective lens (a plurality of dioptric lenses 208, reflecting member 207, concave reflecting surface 206) and is blocked by the blocking member 213a provided to the first relay lens 203. Also in FIGS. 13B and 13C, the specularly reflected light is blocked by the blocking member 203b and the turn-back mirror 203c provided to the spatial filter 209 and detection of defects is possible by the detectors 201b and 201c with high S/N.

Next, FIGS. 14A to 14C show the optical path of the scattered light in each of the embodiments. In FIG. 14A, the scattered light from the wiring short-circuit unit 503, 504 on the wafer surface 1 is transmitted through the catadioptric objective lens including a plurality of dioptric lenses 208, the concave reflecting surface 206 and the reflecting member 207 and is once focused by the imaging lens 204. However, it is not blocked by the blocking member 213a provided to the first relay lens 203 shown in FIG. 13A, is again focused and detected by the detector 201a. Also in FIGS. 14B and 14C, the scattered light is not blocked by the blocking member 213b and the turn-back mirror 213c but is again focused and detected by the detectors 201b and 201c.

Next, a defect inspection device for detecting foreign matters adhering to or occurring on a substrate by using the inspection optical system represented in each of the embodiments described above will be explained with reference to FIGS. 15A and 15B.

The defect inspection device shown in FIG. 15A includes a stage unit 300 having a substrate table 304, xyz stages 301, 302 and 303 and a stage controller 305, an illumination optical system having an illumination light source 211 and a turn-back mirror 205, an inspection optical system 200 having detectors 201 and 251, relay lenses 202 and 203, an imaging lens 204, a half mirror 252, a concave reflecting surface 206, a blocking member 207 and a dioptical lens group having a plurality of dioptric lenses, a computation processing unit 400 for acquiring digital images by using digital signals that are obtained by A/D conversion of the outputs from unidimensional detectors 201 and 251 and stage driving signals obtained from the stage controller 305, and detecting the defects on the substrate by processing the digital images, and an overall control unit 417.

The inspection optical system 200 has a construction similar to that of the inspection optical system of the first embodiment shown in FIG. 1 but is different in that the scattered light from the wafer 1 is detected by the two detectors 201 and 251 through the half mirror 252. The detectors 201 and 251 acquire polarized light of the P wave and S wave depending on the difference of shapes of the foreign matters. The detector may be one or more than three but the analysis can be made more strictly by acquiring both P wave and S wave.

The optical image acquired by the inspection optical system shown in FIG. 15A is received and is subjected to photoelectric conversion and the resulting signal is sent to the computation processing unit 400.

Next, the processing by the computation processing unit 400 will be explained with reference to FIG. 15B. The computation processing unit 400 includes an A/D converter 4001 for A/D converting the detected image signal outputted from the detector 201, a data storage unit 4002 for storing the digital image signal A/D converted by the A/D converter 4002, a threshold value computation processing unit 4003 for executing a threshold computation processing on the basis of the A/D converted detected image signal from the detector 201, a foreign matter detection processing circuit unit 4007 for executing a foreign matter detection processing on the basis of the detected image signal 4110 acquired from the data storage unit 4002 and the threshold value image signal 4120 acquired from the threshold value computation unit 4003, and a feature quantity computation circuit unit 4008 for computing a feature quantity of the defect detected by the foreign matter detection processing circuit unit 4007. The information of the feature quantity of the defect detected and acquired from the feature quantity computation circuit 4008 is sent to the overall processing unit 4010. On the other hand, the signal acquired by the detector 251 is digitized similarly by the A/D converter 4201 and is branched. One of the signals branched is stored in the data storage unit 4202 and the other is inputted to the threshold value computation processing unit 4203. The detected image signal 4310 outputted from the data storage unit 4202 and the threshold value image signal 4320 outputted from the threshold value computation processing unit 4203 are inputted to the foreign matter detection processing unit 4207, where they are subjected to the foreign matter detection processing. The image of the defect so detected is processed by the feature quantity computation circuit unit 4208 and the feature quantity is computed. The information of the feature quantity acquired from the feature quantity computation circuit 4208 is sent to the overall processing unit 4010 and is synthesized with the information of the feature quantity of the defect acquired from the image detected by the detector 251 and is classified into various kinds of defects such as large foreign matters, small foreign matters, pattern defects, surface scratches of the substrate, and so forth.

The computation processing unit 400, the illumination light source 211 and the stage controller 305 are connected to and controlled by the overall control unit 417.

The defect inspection device shown in FIGS. 15A and 15B can correct chromatic aberration resulting from a plurality of wavelengths and can reduce the change of light power resulting from the change of the film thickness of the wafer 1. The concave reflecting surface 206 having the center hole and the convex blocking member 207 having the light transmission region 237 at its center can achieve vertical illumination and can illuminate the wiring short-circuit unit with sufficient intensity. As a result, the short-circuit defect can be detected. Furthermore, the specularly reflected light transmitted through the light transmission region 237 formed at the center of the convex blocking member 207 is blocked by the blocking member 213 and the flare component can be removed. Therefore, detection of the defect can be made with a high S/N. High NA can be achieved because a large space need not be secured between the wafer 1 and the dioptric lens group 208.

Incidentally, the inspection optical system in the defect inspection device shown in FIGS. 15A and 15B is similar to the inspection optical system of the first embodiment shown in FIG. 1 but the inspection optical system of the second or third embodiment shown in FIG. 2 or 3 or other inspection optical systems having similar functions may also be used.

Next, a construction obtained by adding the illumination optical system 100 and the detection optical system 200b to the inspection optical system 200a shown in FIG. 15A is shown in FIG. 16A as a modified example of the construction of the defect inspection device shown in FIG. 15A. In FIG. 16A, two optical systems are installed, that is, the inspection optical system 200a arranged substantially vertically with respect to the wafer surface 1 and the inspection optical system 200b arranged in an inclined direction.

A method for detecting the defects on the wafer 1 in the construction described above will be explained.

The inspection optical system 200a detects the scattered light by the method similar to that of the inspection optical system 200 shown in FIG. 15A. Only one each detector 201a, 201b is provided to each of the inspection optical systems 200a and 200b in FIG. 16A but a plurality of detectors may be provided, too, and the number can be decided arbitrarily. Next, a method for detecting the scattered light by the illumination optical system and the detection optical system 200b will be explained. The laser beam emitted from the illumination light source 101 of the illumination optical system 100 is emitted slantingly in the horizontal direction of the wafer 1 through the convex lens 102, the concave lens 103, the grating 104 and the mirror 105. The scattered light from the wafer 1 by the radiation of the illumination optical system 100 is focused by the detector 201b through a plurality of dioptric lenses 208b constituting the detection optical system 200b arranged slantingly with respect to the wafer surface 1, the reflecting member 207b having the light transmission region at the center, the concave reflecting surface 206b having the center hole, the imaging lens 204b and the relay lenses 202b and 203b and the optical image is received and photo-electrically converted. When the inspection optical systems are arranged at a plurality of positions, a plurality of the scattered light scattered in the directions of different elevations with respect to the wafer 1 can be individually detected and classification performance of the defects can be improved by processing and synthesizing these signals. The computation processing unit 400 shown in FIGS. 16A and 16B has the construction similar to that of the computation processing unit shown in FIGS. 15A and 15B. The computation processing unit 400, the illumination light sources 101 and 211 and the stage controller 305 are connected to and controlled by the overall control unit 417.

The defect inspection device shown in FIGS. 16A and 16B can correct chromatic aberration and can reduce the change of light power resulting from the change of the film thickness of the wafer 1. Because the light transmission region 237 is formed in the turn-back mirror 205 and at the center of the reflecting member 207, vertical illumination can be made and the wiring short-circuit unit can be illuminated with sufficient intensity. As a result, the short-circuit defect can be detected. Because the specularly reflected light from the wafer 1 is blocked by the blocking member in front of the detectors 201a and 201b and the flare component can be removed, detection of the defect can be made with high S/N. Because a plurality of the scattered light scattered at different elevations in the substantial vertical direction of the wafer surface 1 can be individually detected, classification performance of the defects can be improved by processing and synthesizing these signals. The scattered light of the foreign matters on the wiring can be caught more easily by illumination of inclined incidence and the scattered light of the foreign matters below the wiring can be caught more easily by illumination of vertical incidence. Therefore, the suitable illumination method can be selected in accordance with the characteristics of the defects.

The inspection optical system 200 of the defect inspection device shown in FIGS. 15A and 16B may have a movable construction with the wafer 1 as the center as shown in FIG. 17. FIG. 16A shows a defect inspection device when the inspection optical system shown in FIG. 15A is moved in the inclined direction with respect to the wafer 1. When the position of arrangement of the inspection optical system is changed in accordance with the characteristics of the defects to be detected, the classification performance of the defects can be improved.

In the construction in which the spatial filter 209 having the turn-back mirror 213 is arranged in front of the relay lens 203 shown in FIG. 18, the turn-back mirror 213 can play both roles of accomplishing vertical illumination and blocking the specularly reflected light. Therefore, it is possible to achieve space saving and the reduction of the cost of production in the manufacturing process of the defect inspection device.

It should be further understood by those skilled in the art that although the foregoing description has been made on embodiments of the invention, the invention is not limited

Figure 1:
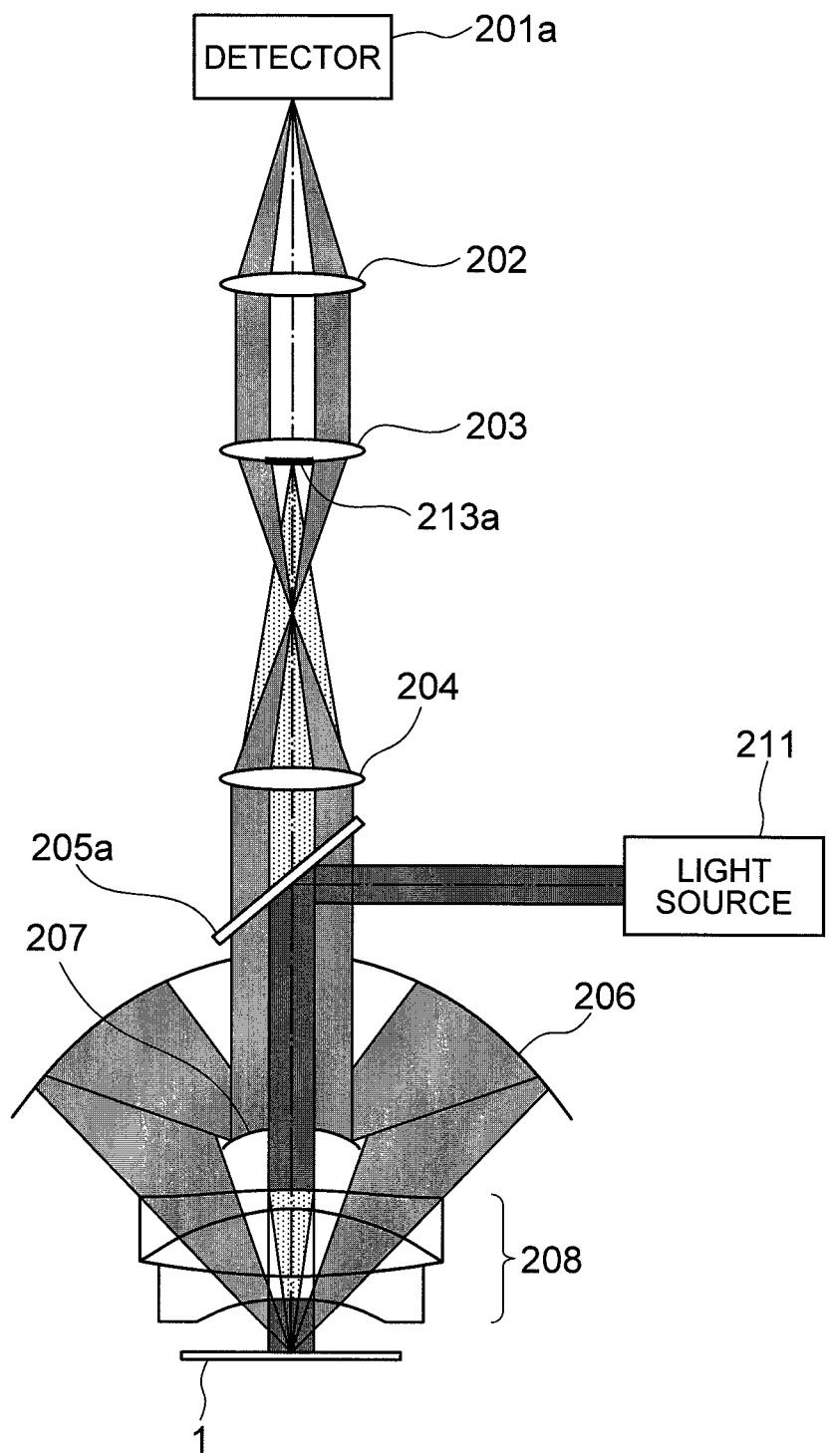
FIG. 1 shows an inspection optical system according to a first embodiment of the invention.
Figure 2:
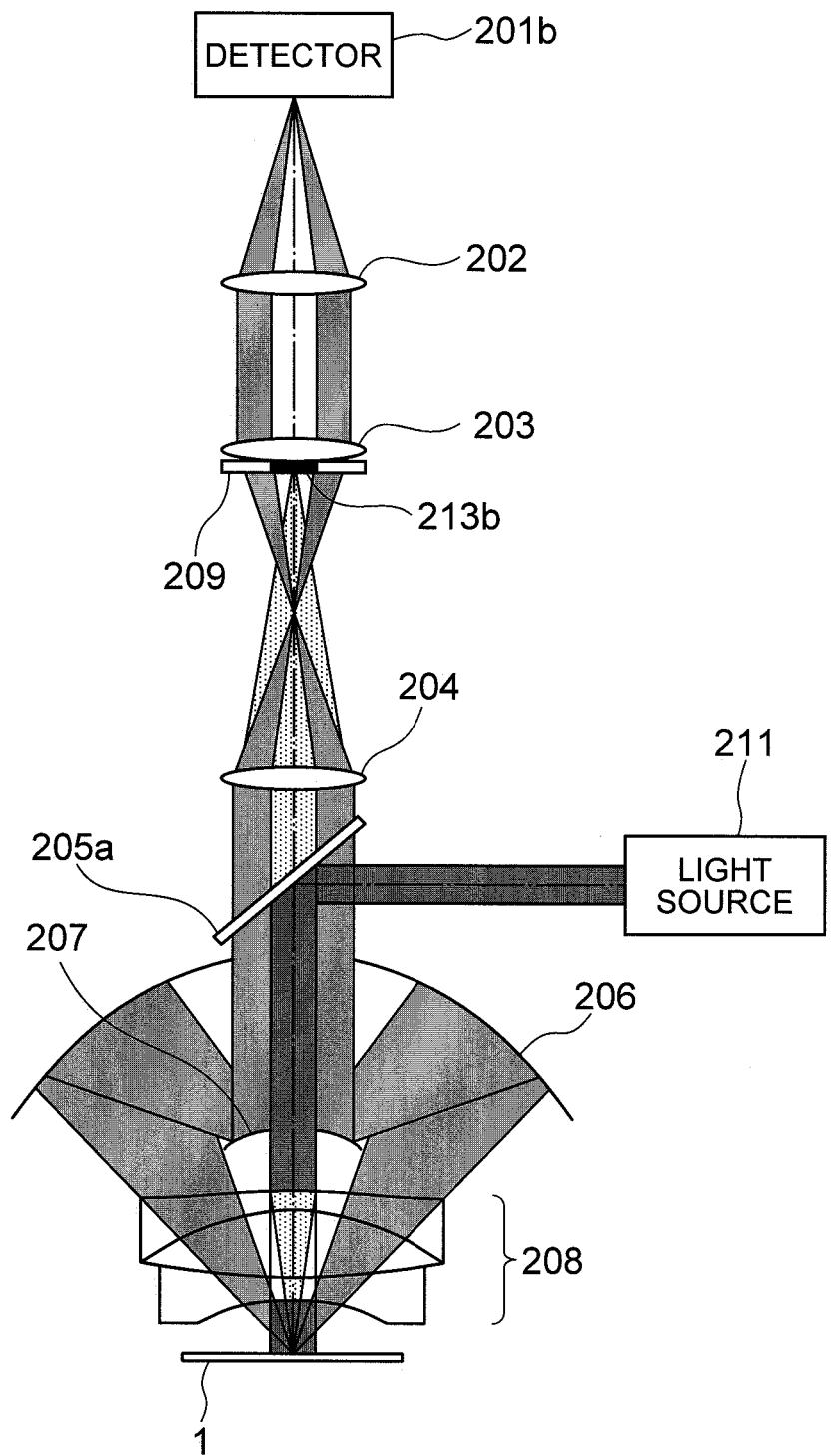
FIG. 2 shows an inspection optical system according to a second embodiment of the invention.
Figure 3:
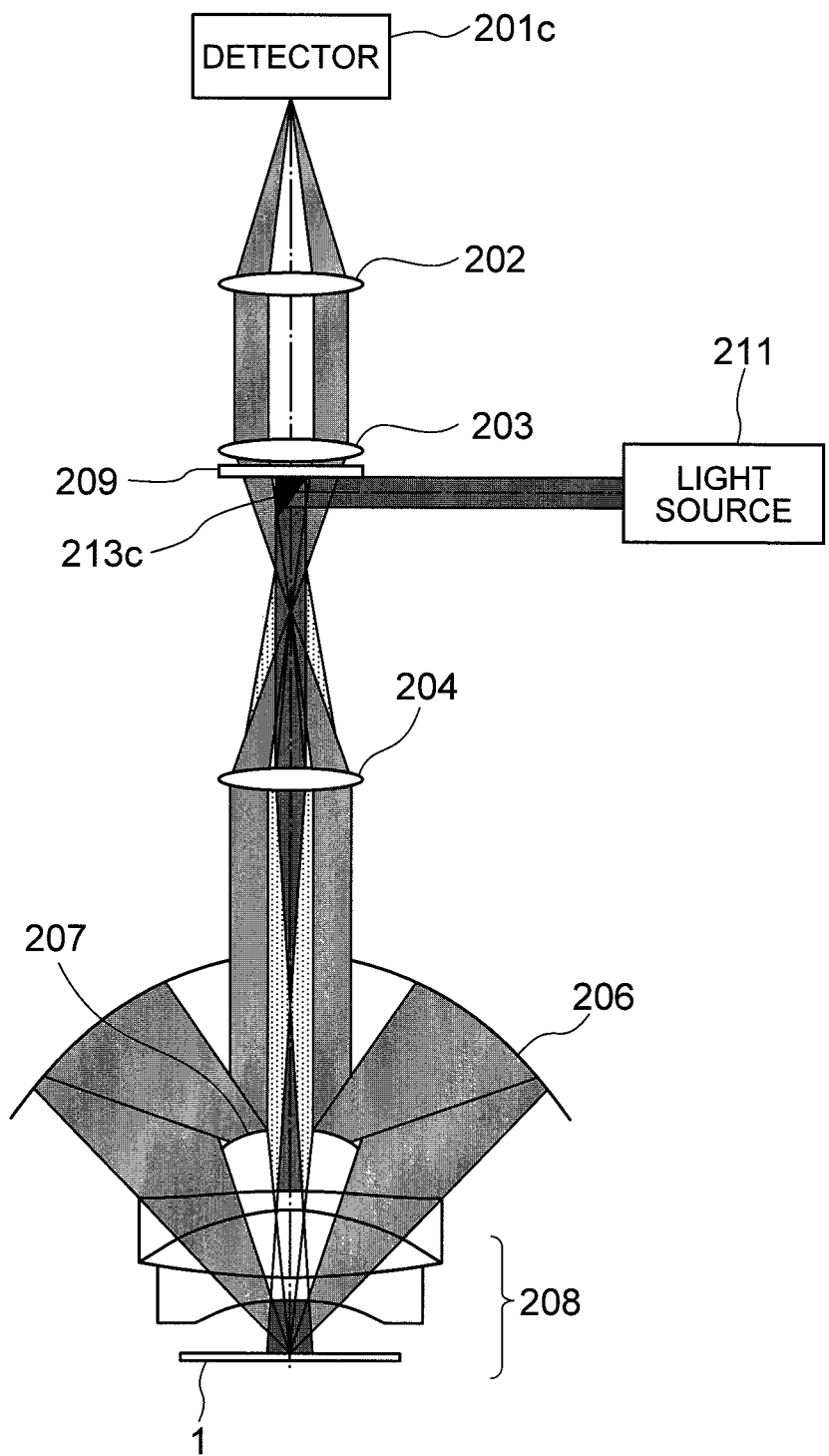
FIG. 3 shows an inspection optical system according to a third embodiment of the invention.
Figure 4:
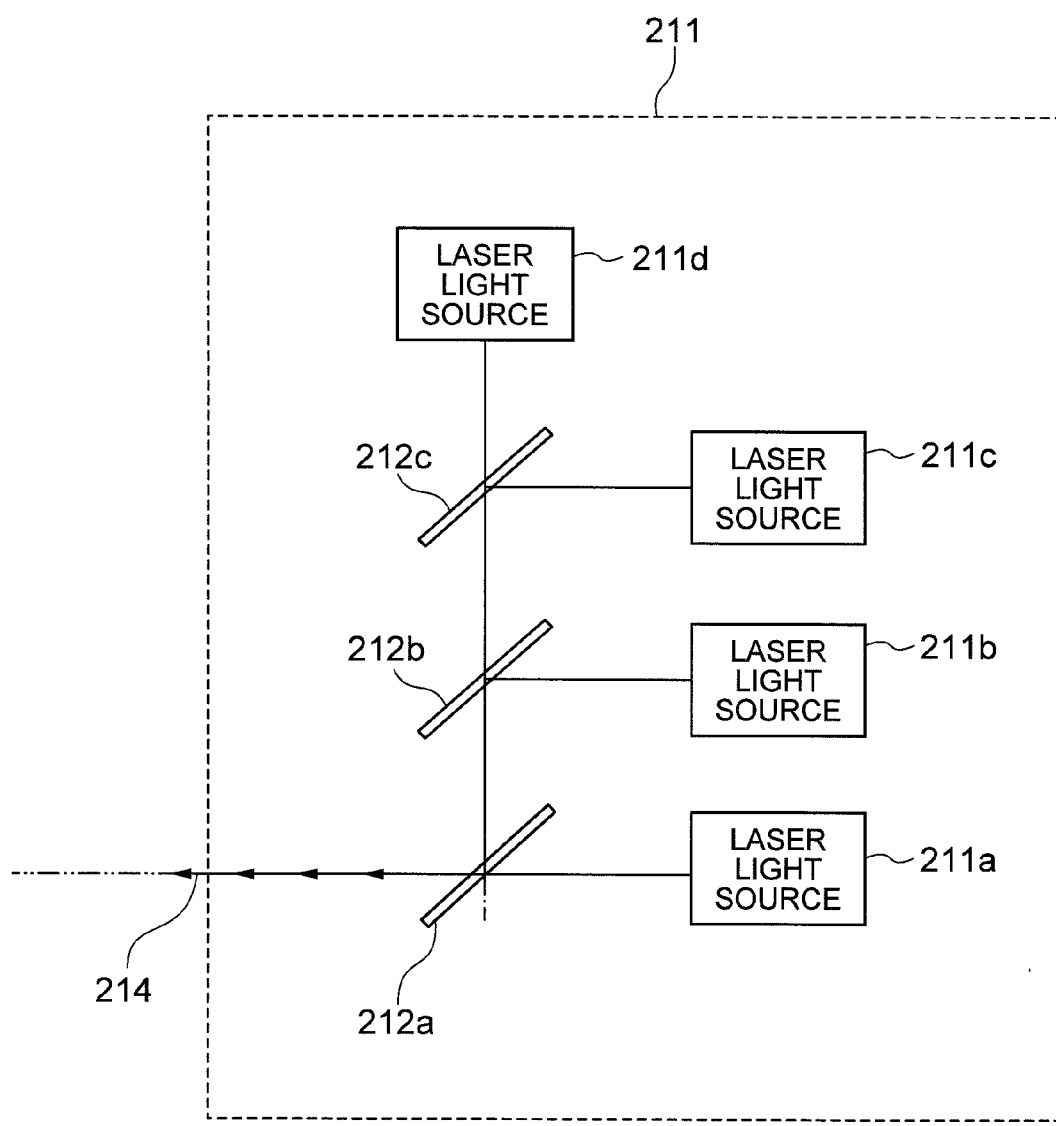
FIG. 4 is an explanatory view of an illumination light source for executing radiation of a plurality of wavelengths.
Figure 5A:
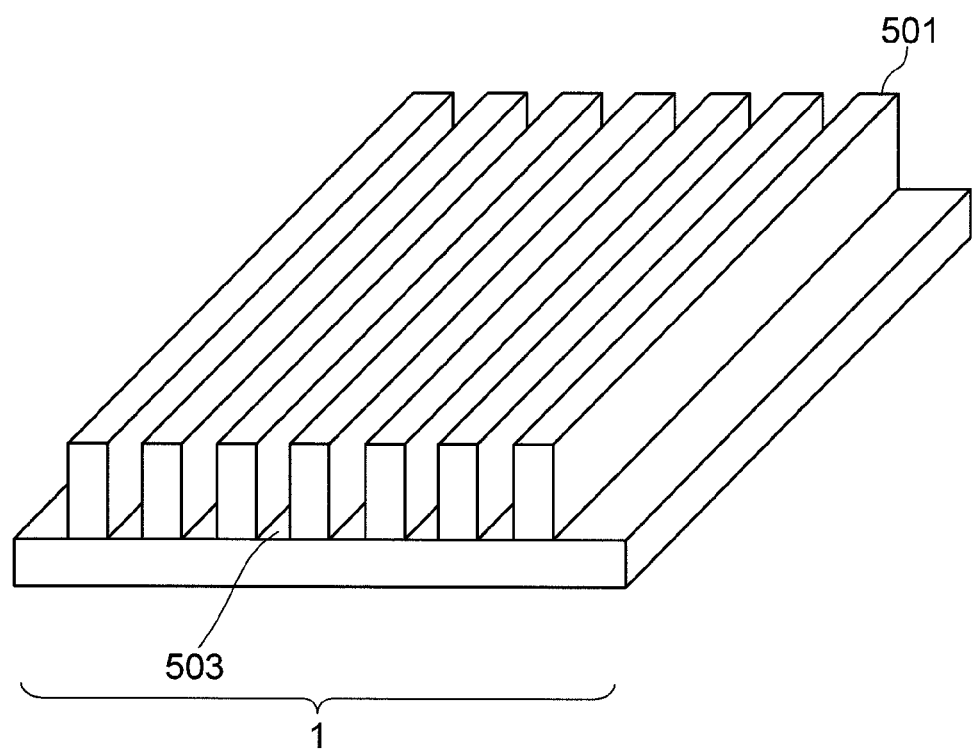
FIG. 5A shows a first example about a wafer surface.
Figure 5B:
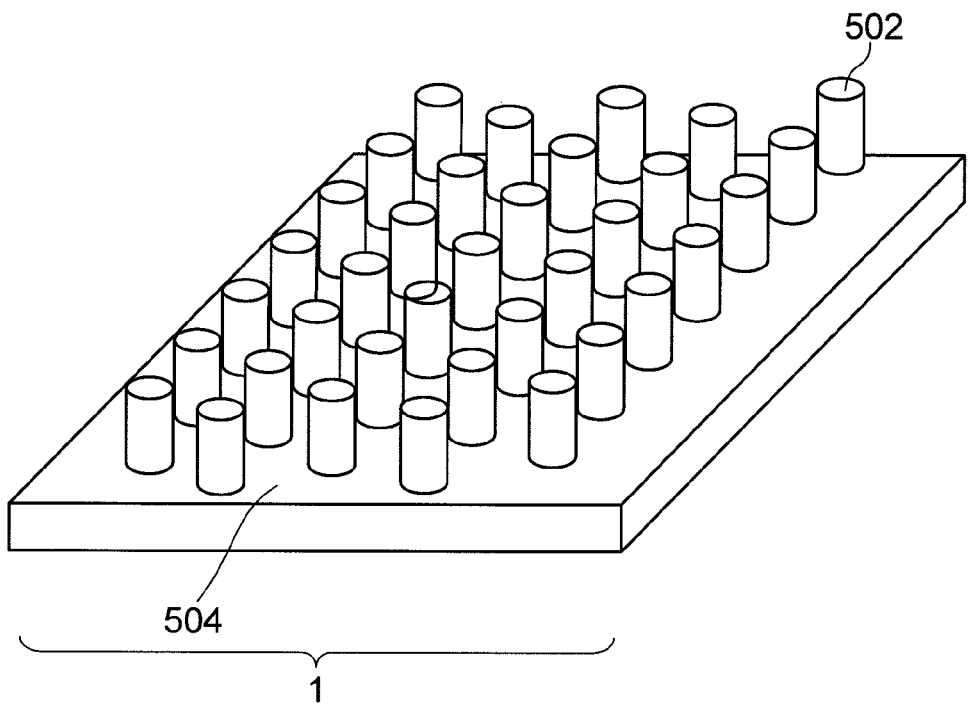
FIG. 5B shows a second example.
Figure 6A:
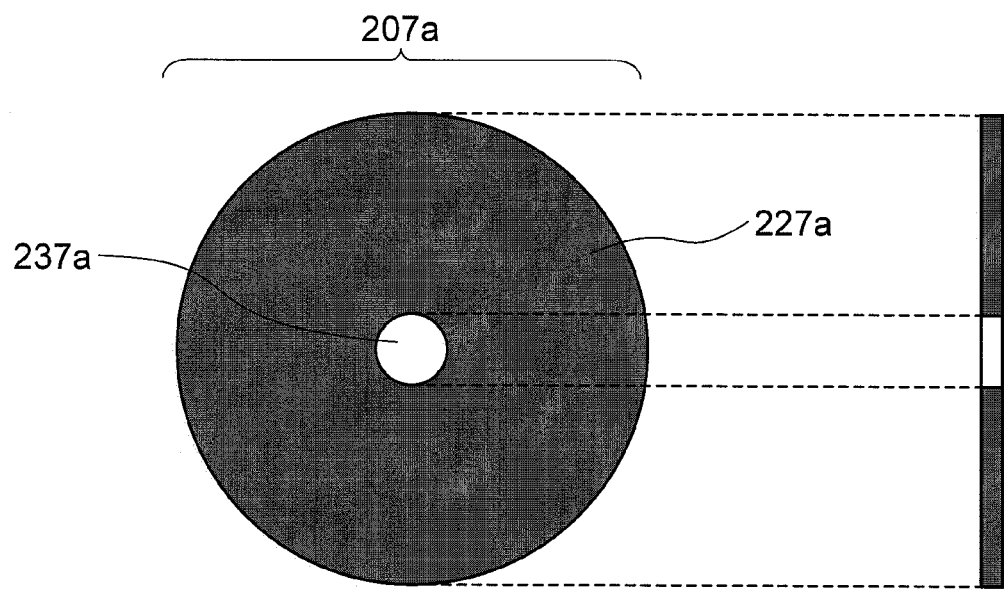
FIG. 6A is an explanatory view of a convex reflecting member.
Figure 6B:
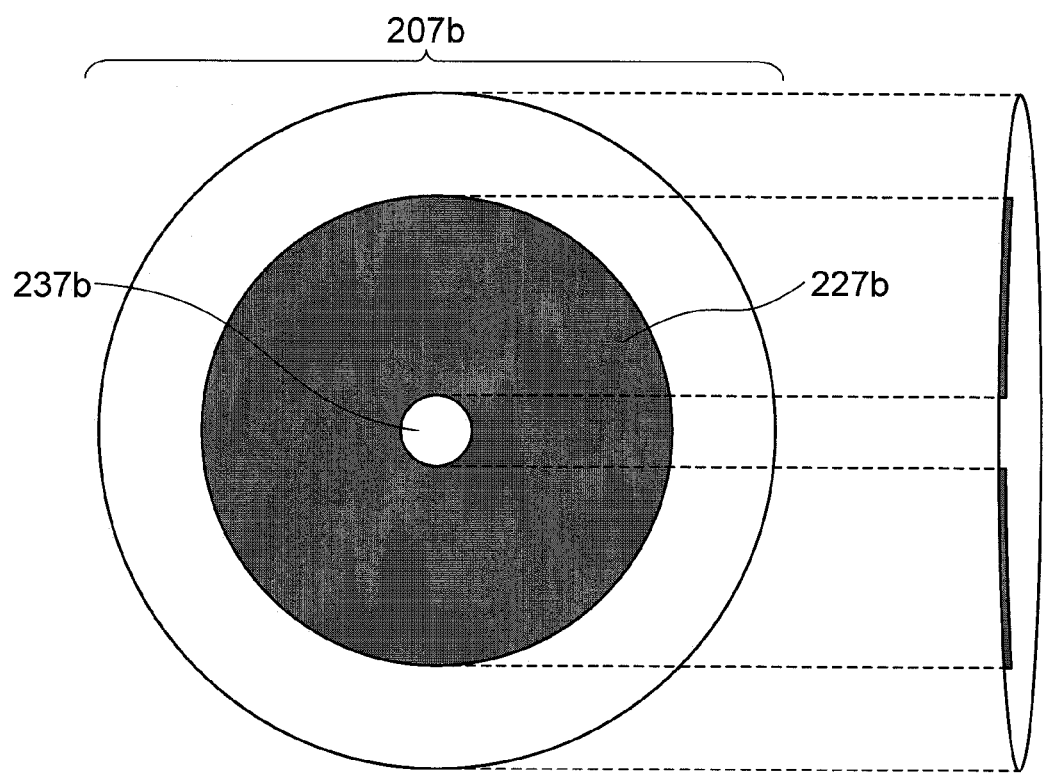
FIG. 6B shows a modified example of the convex reflecting member.
Figure 7:
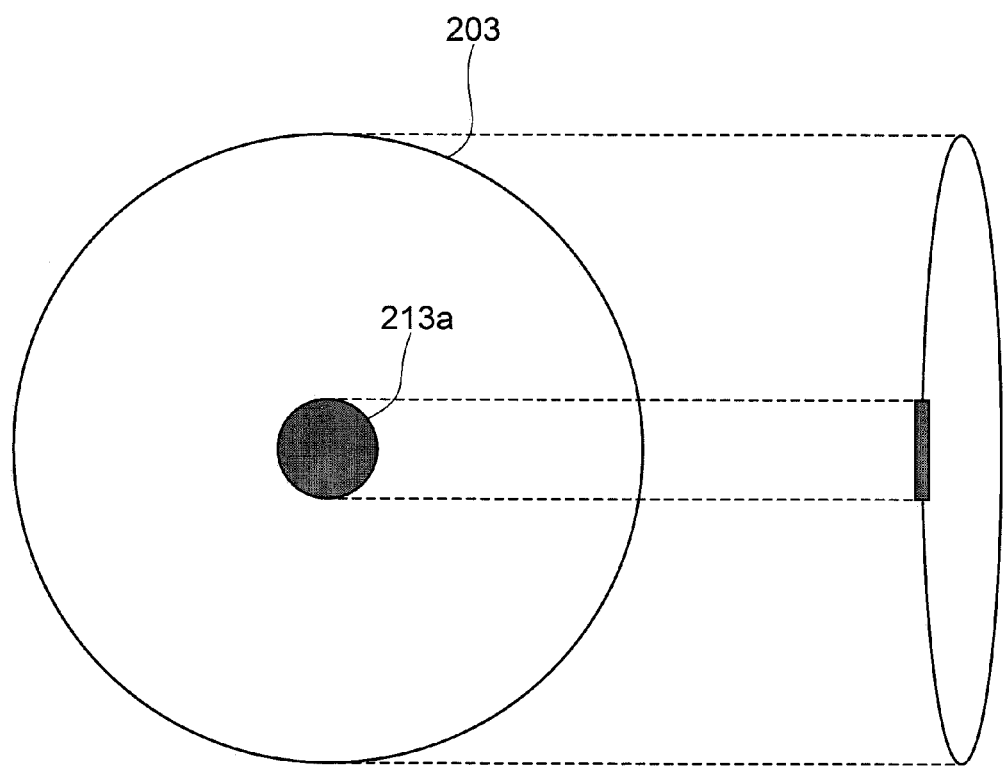
FIG. 7 shows a spatial filter having a first relay lens and a blocking member in the first embodiment.
Figures 8A, 8B:
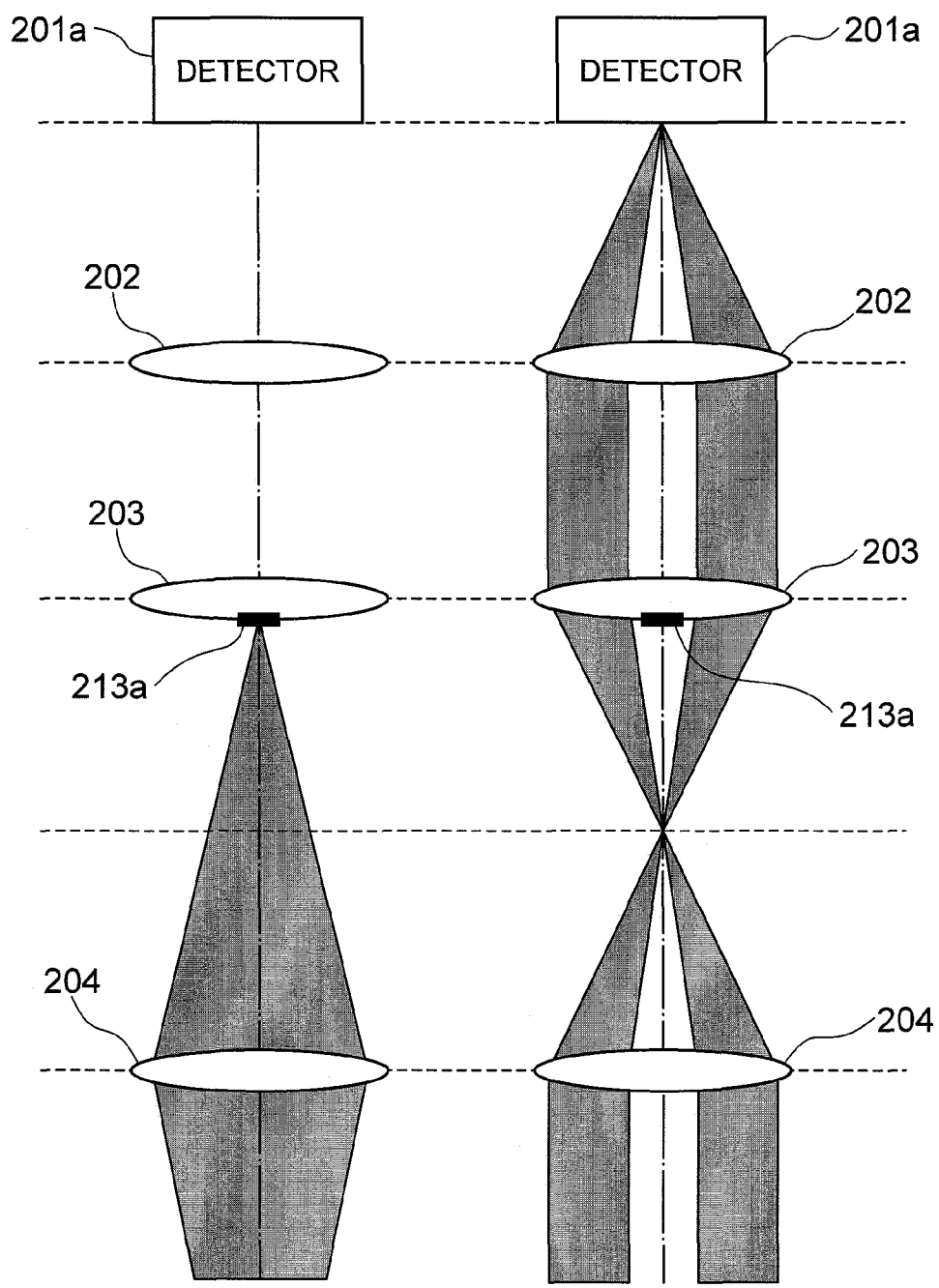
FIG. 8A is an optical path diagram of specularly reflected light in the first embodiment.
FIG. 8B is an optical path diagram of scattered light in the first embodiment.
Figure 9:
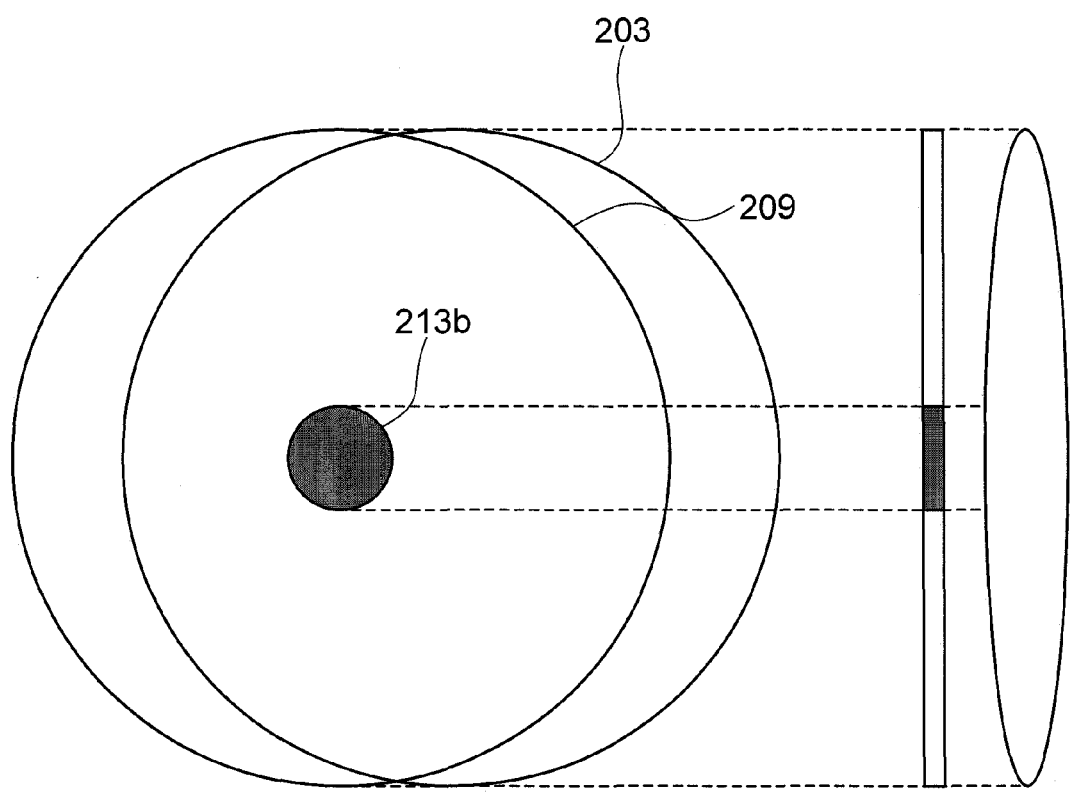
FIG. 9 shows a spatial filter having a first relay lens and a blocking member in the second embodiment.
Figures 10A, 10B:
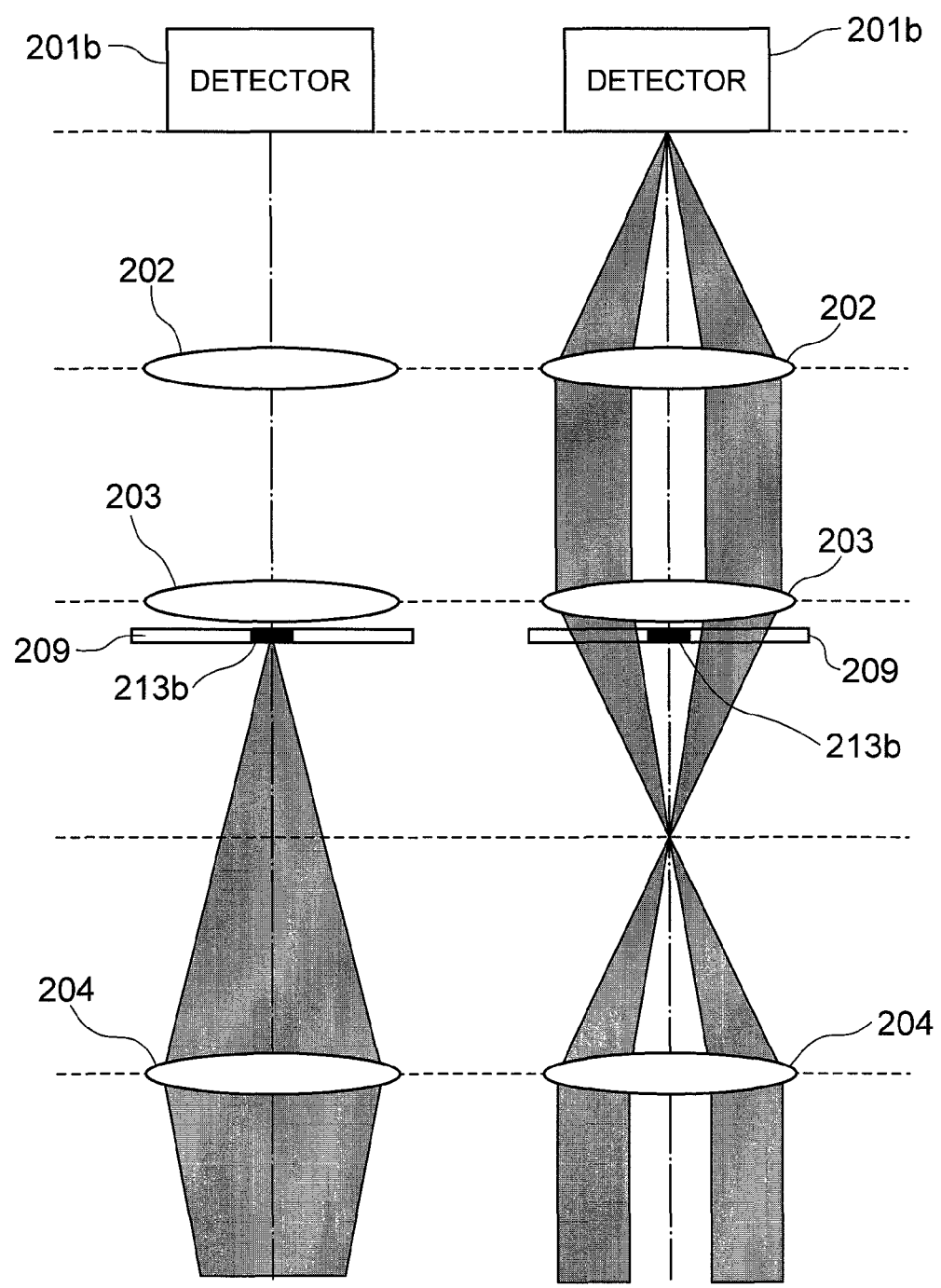
FIG. 10A is an optical path diagram of specularly reflected light in the second embodiment.
FIG. 10B is an optical path diagram of scattered light in the second embodiment.
Figure 11:
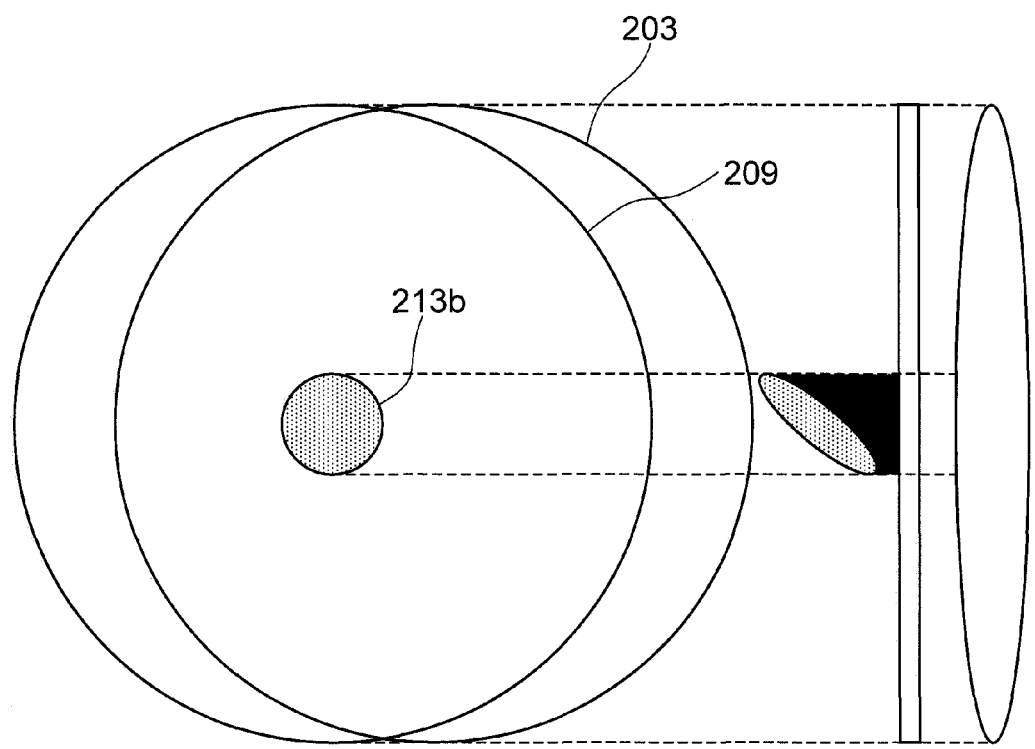
FIG. 11 shows a spatial filter having a first relay lens and a blocking member in the third embodiment.
Figures 12A, 12B:
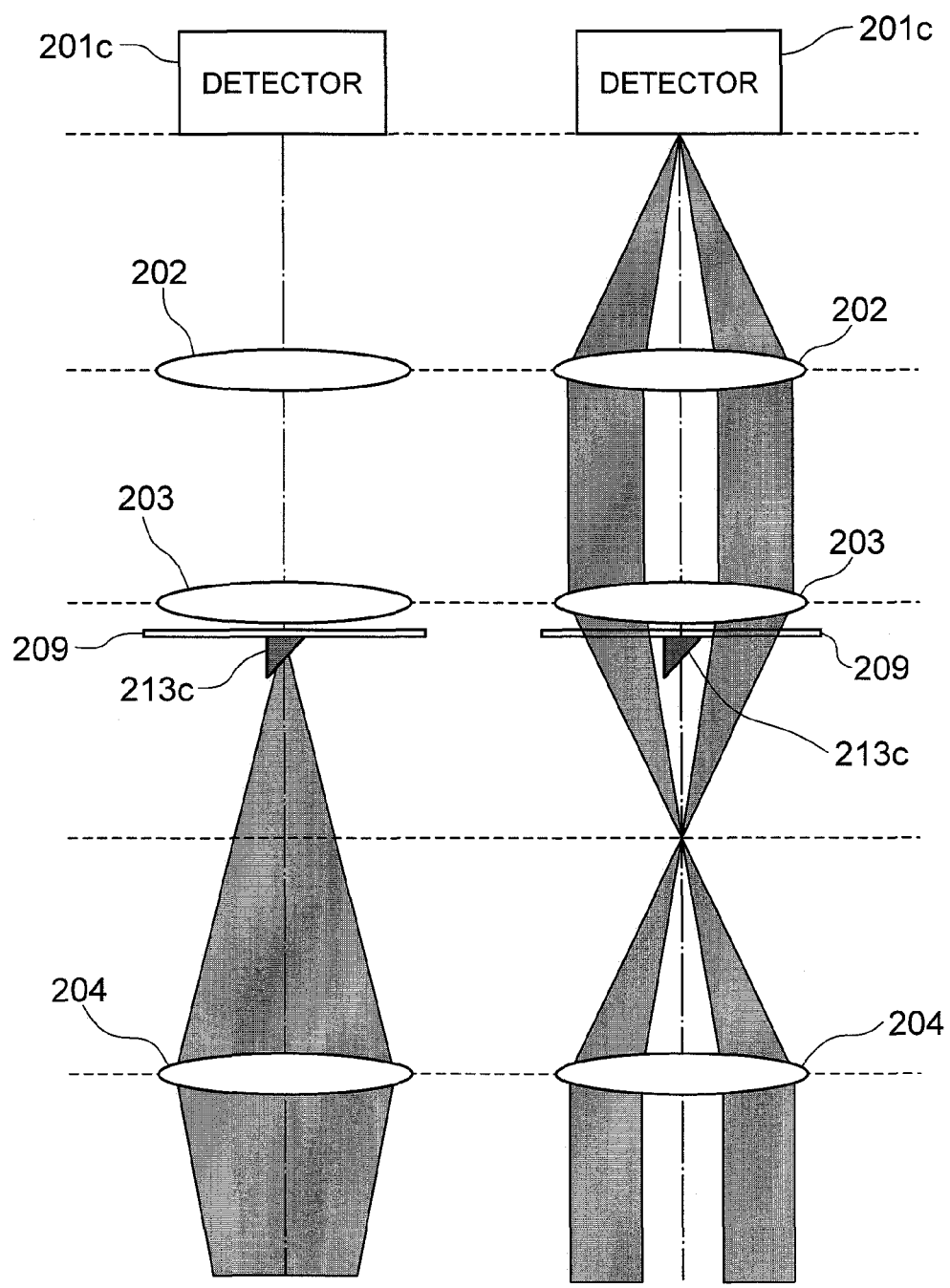
FIG. 12A is an optical path diagram of specularly reflected light in the third embodiment.
FIG. 12B is an optical path diagram of scattered light in the third embodiment.
Figure 13A:
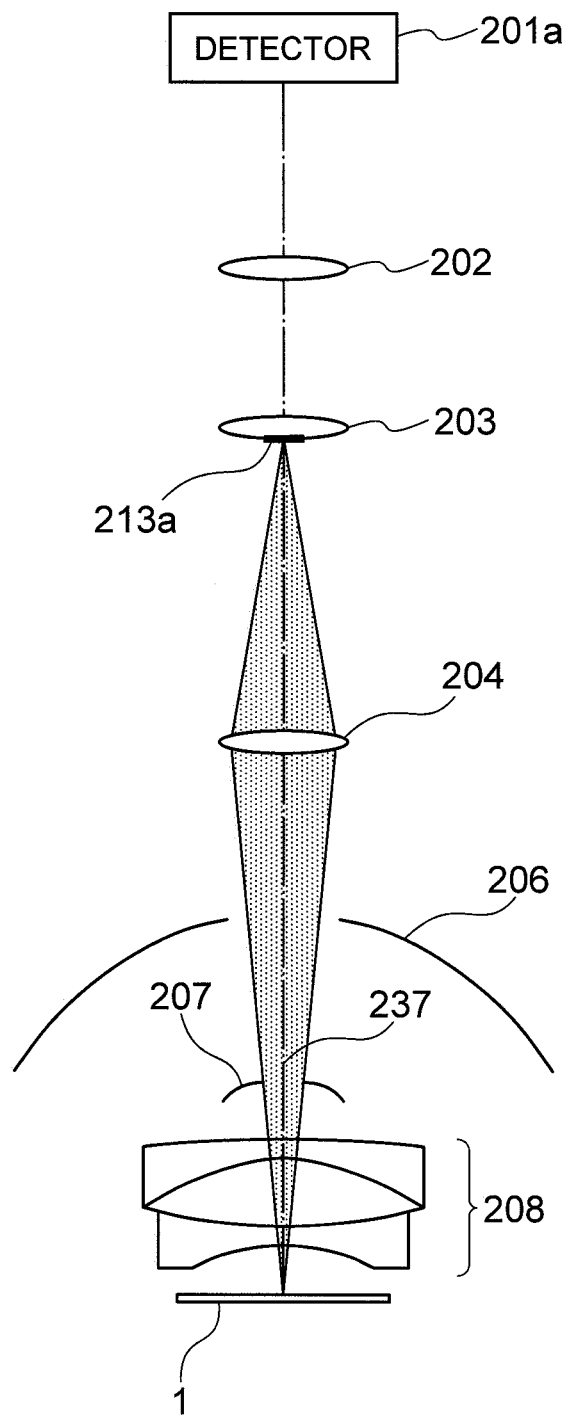
FIG. 13A is an optical path diagram of specularly reflected light of an inspection optical system in the first embodiment.
Figure 13B:
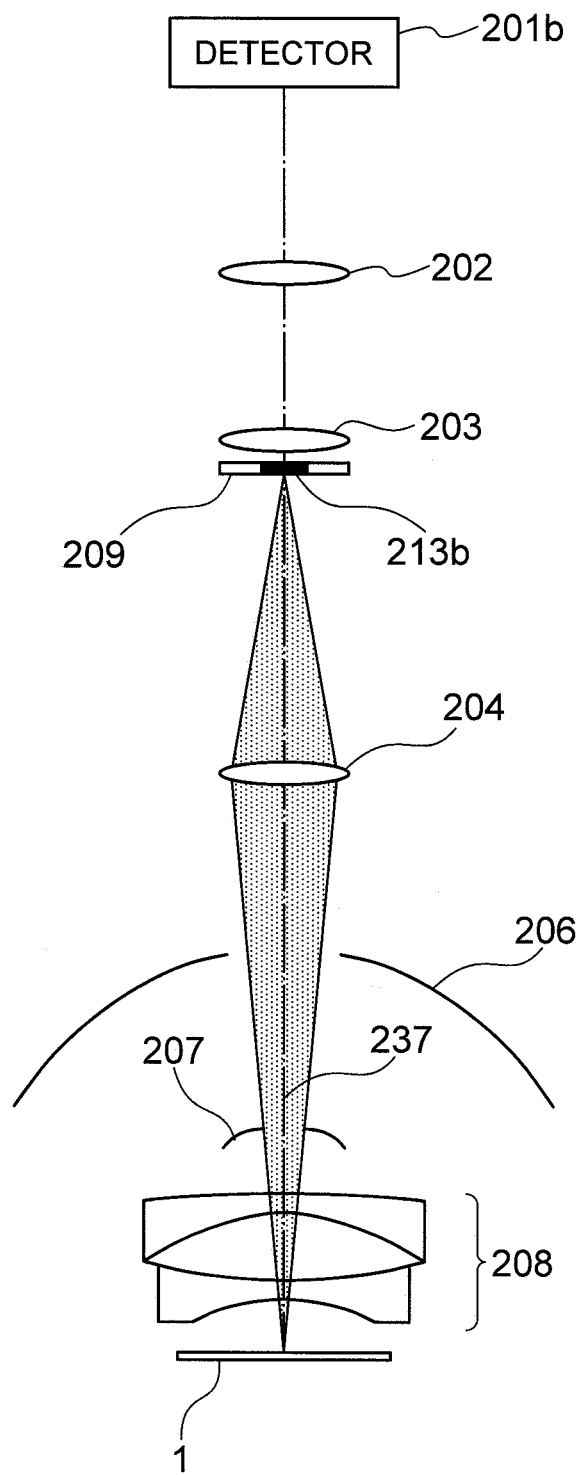
FIG. 13B is an optical path diagram of specularly reflected light of an inspection optical system in the second embodiment.
Figure 13C:
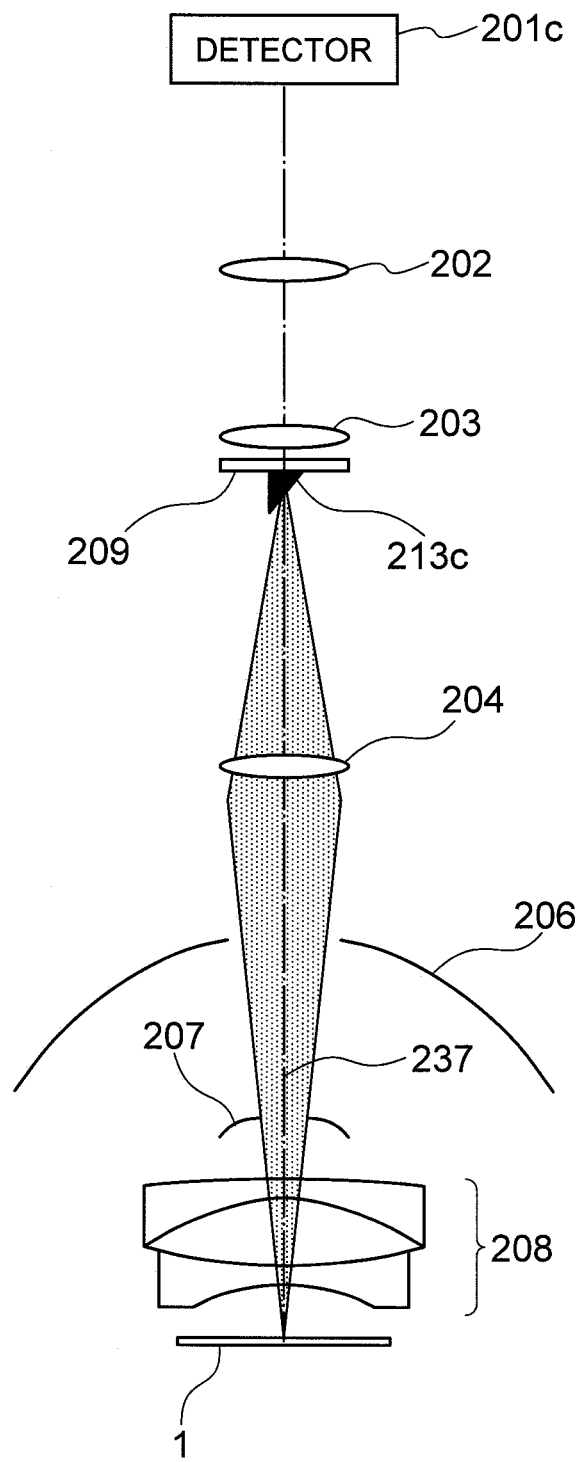
FIG. 13C is an optical path diagram of specularly reflected light of an inspection optical system in the third embodiment.
Figure 14A:
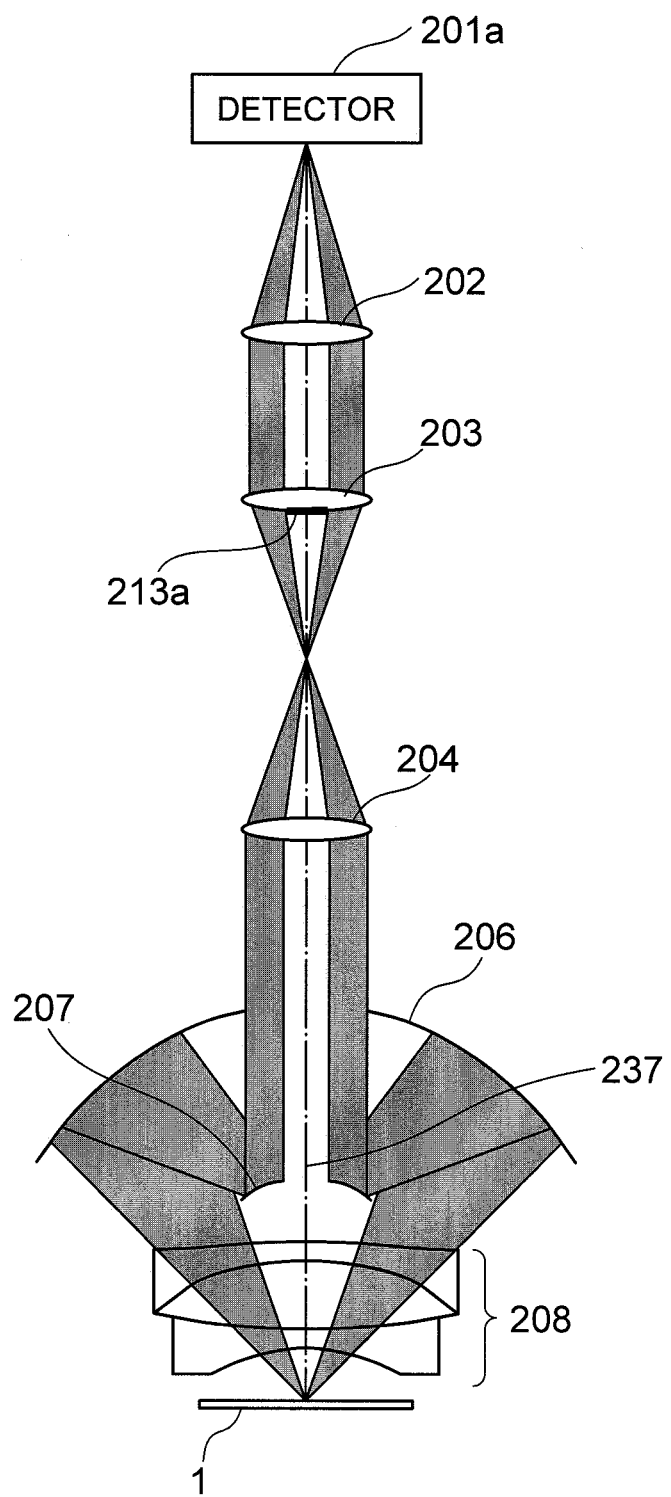
FIG. 14A is an optical path diagram of scattered light of an inspection optical system in the first embodiment.
Figure 14B:
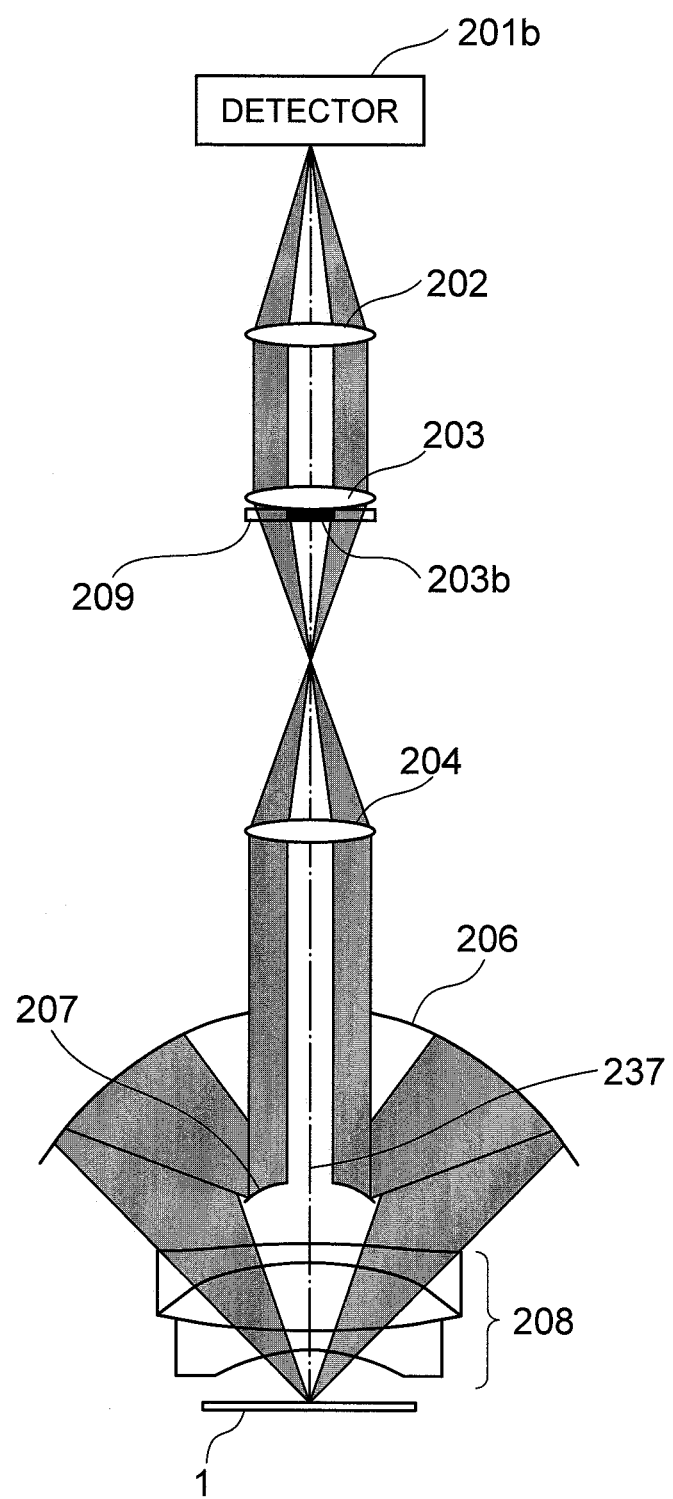
FIG. 14B is an optical path diagram of scattered light of an inspection optical system in the second embodiment.
Figure 14C:
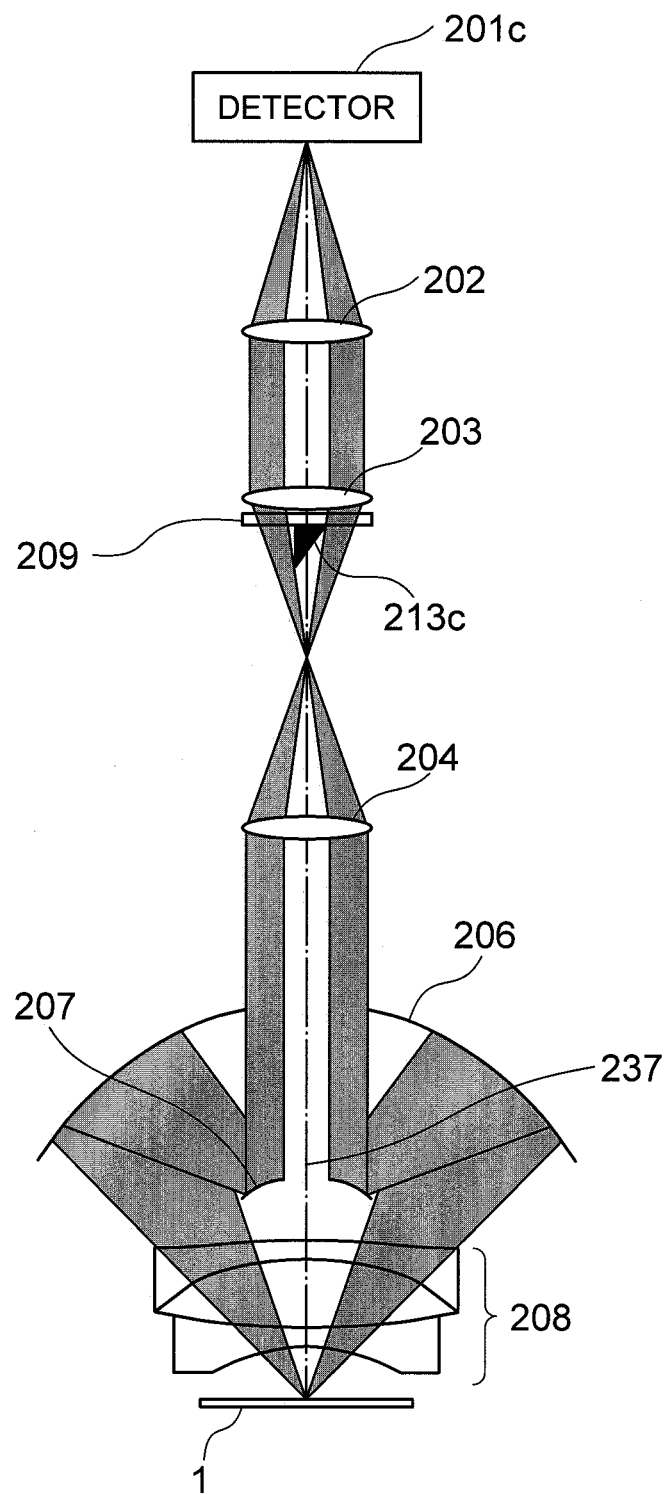
FIG. 14C is an optical path diagram of scattered light of an inspection optical system in the third embodiment.
Figure 15A:
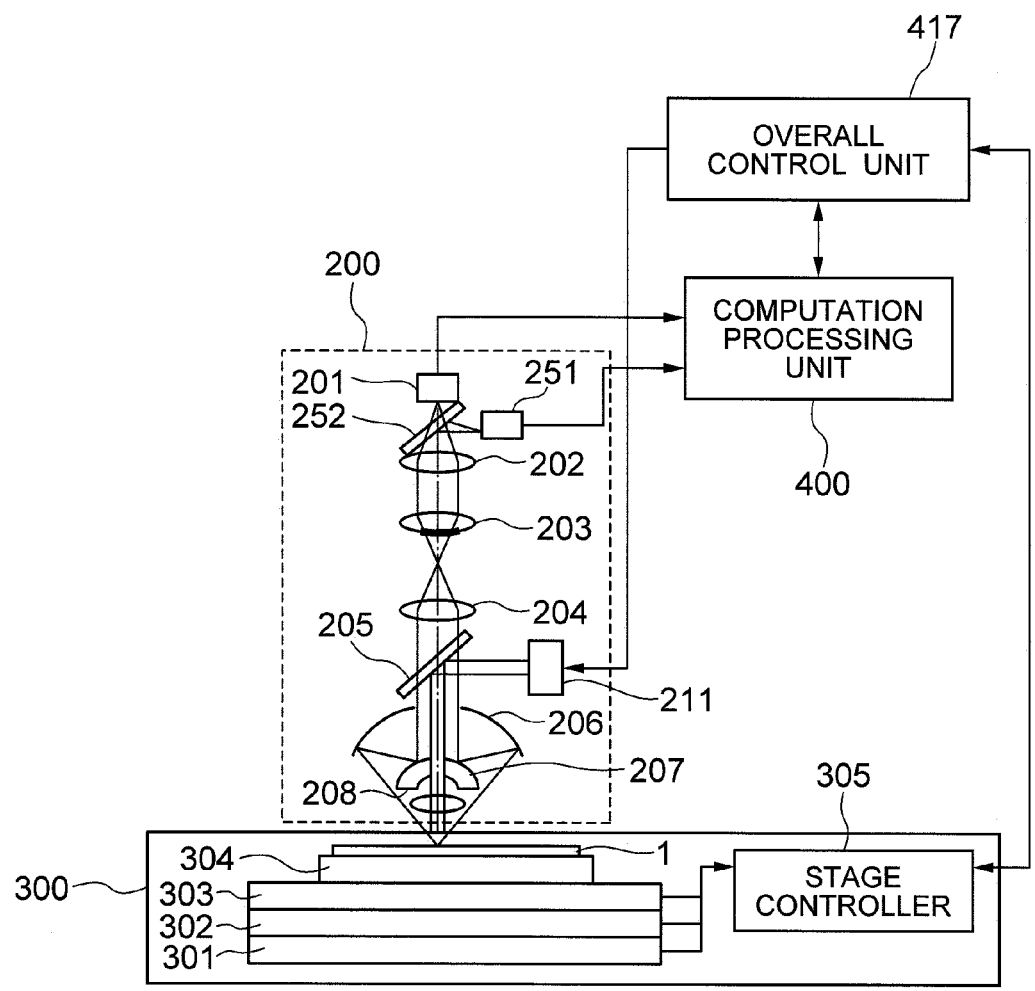
FIG. 15A shows a defect inspection device according to the invention.
Figure 15B:
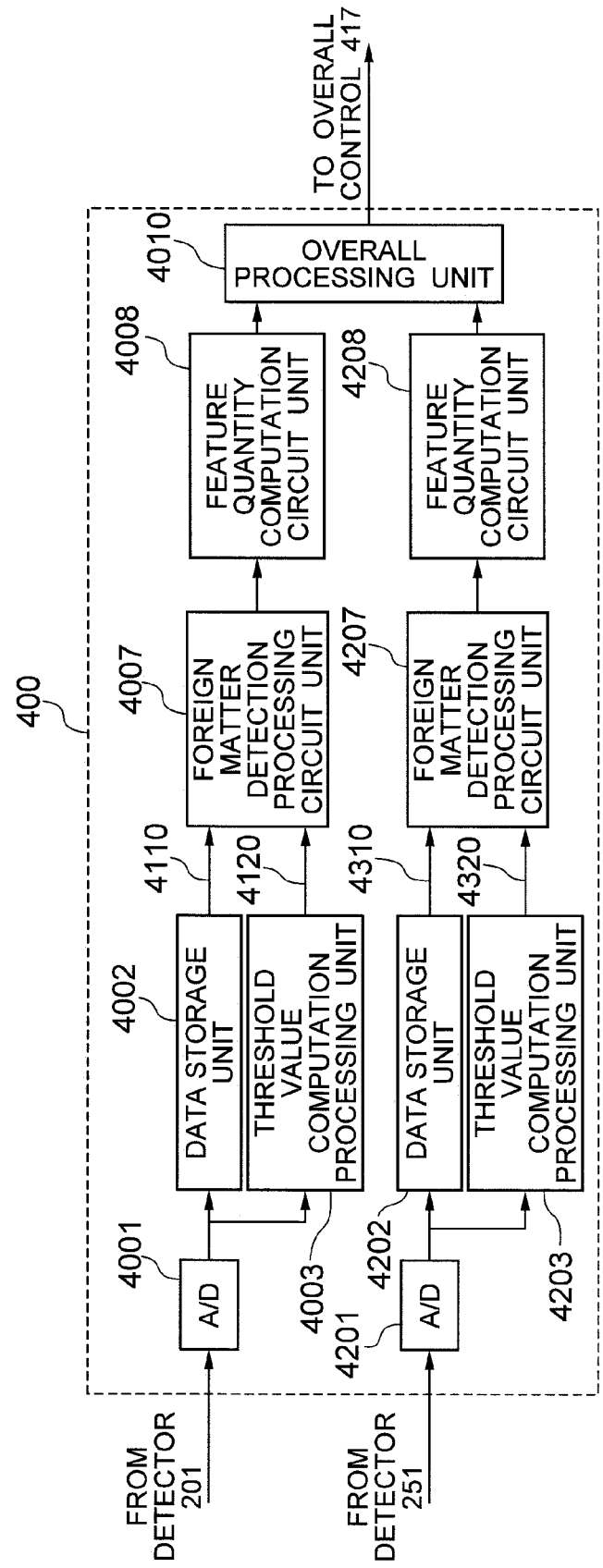
FIG. 15B shows a defect inspection device according to the invention.
Figure 16A:
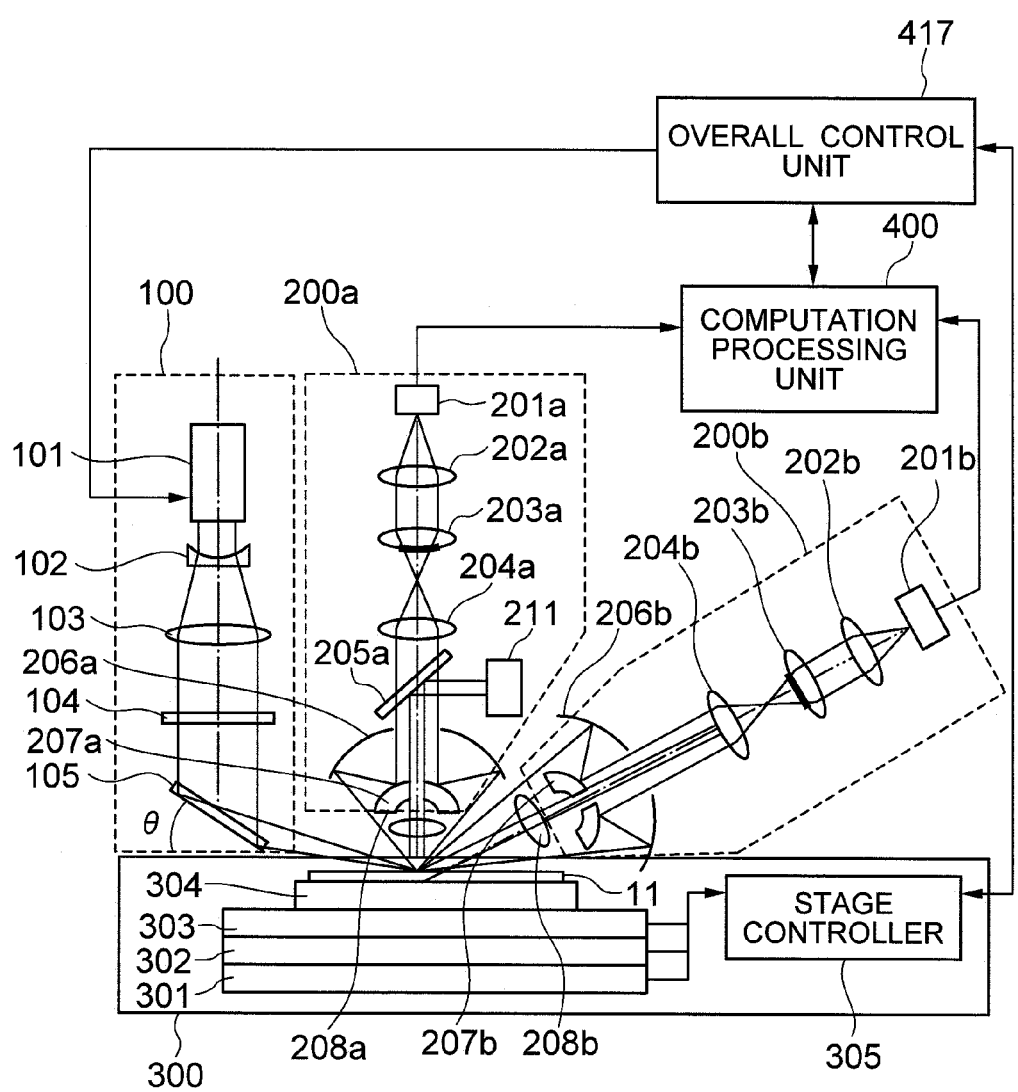
FIG. 16A shows a modified example of the defect inspection device according to the invention.
Figure 16B:
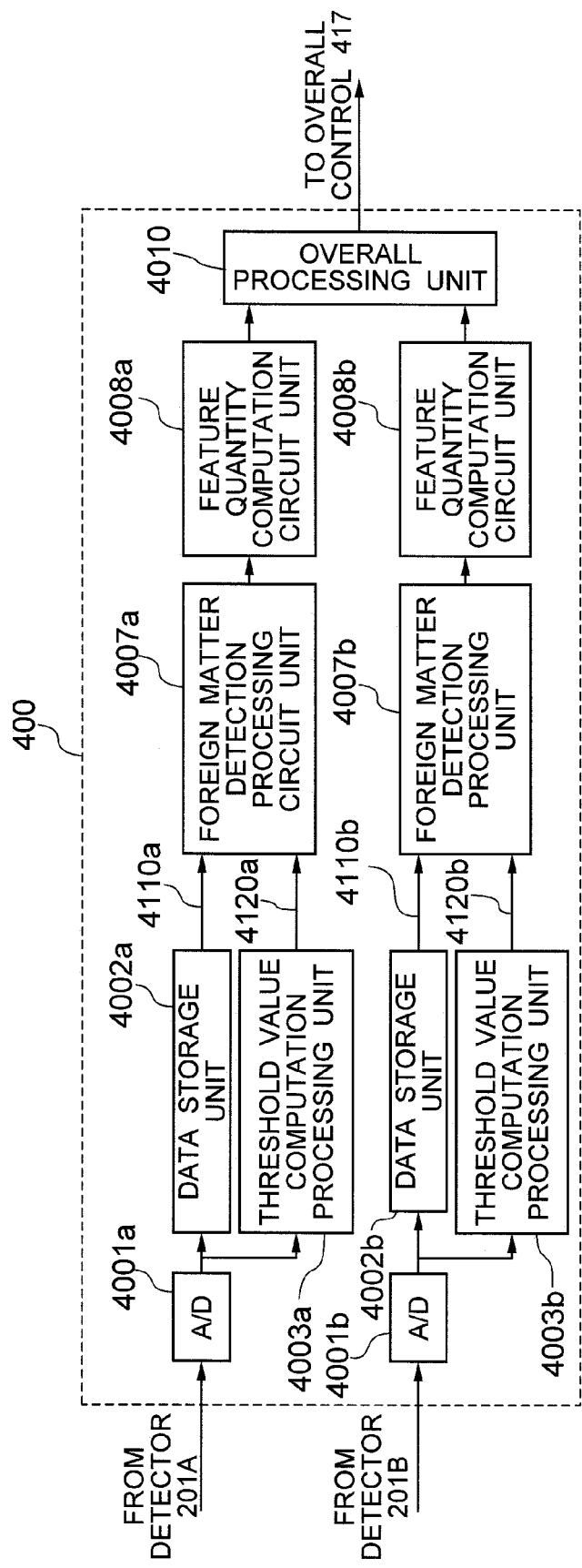
FIG. 16B shows a modified example of the defect inspection device according to the invention.
Figure 17:
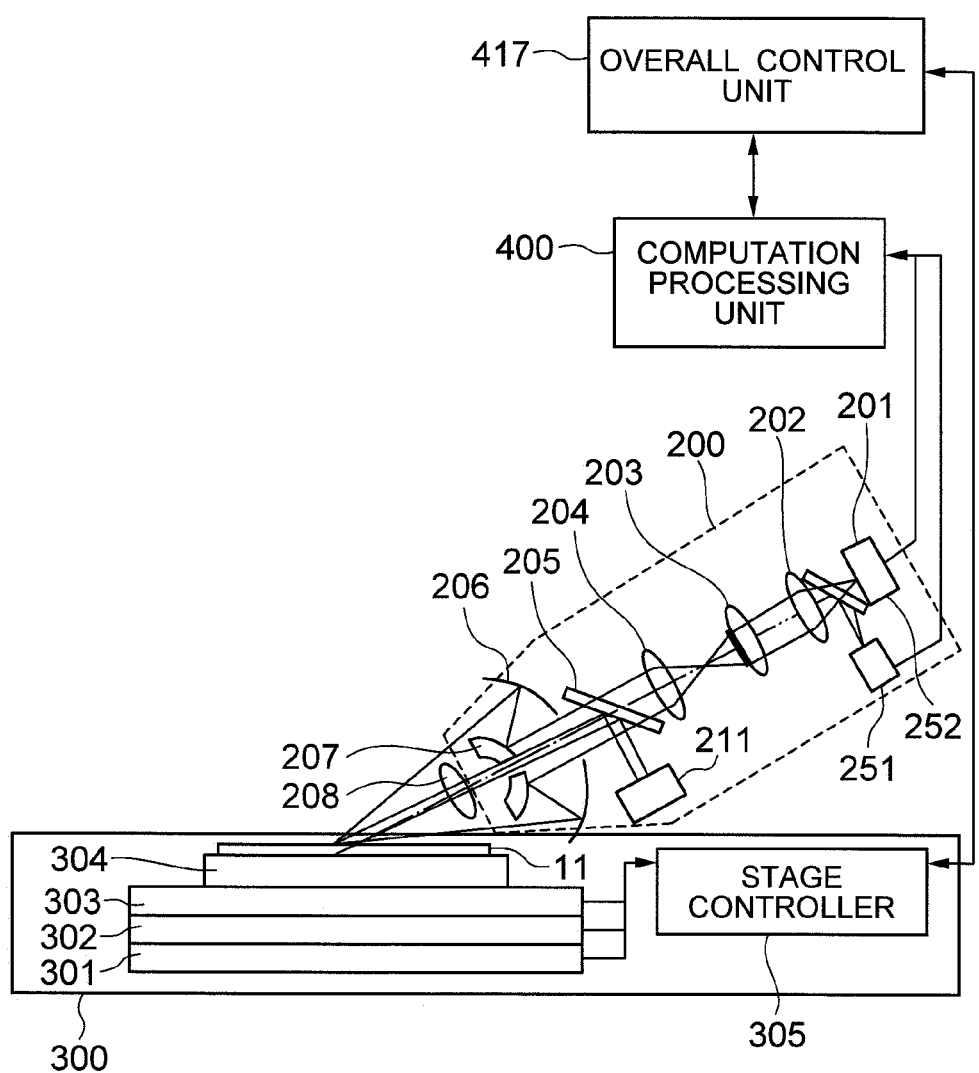
FIG. 17 shows a modified example of the defect inspection device according to the invention.
Figure 18:
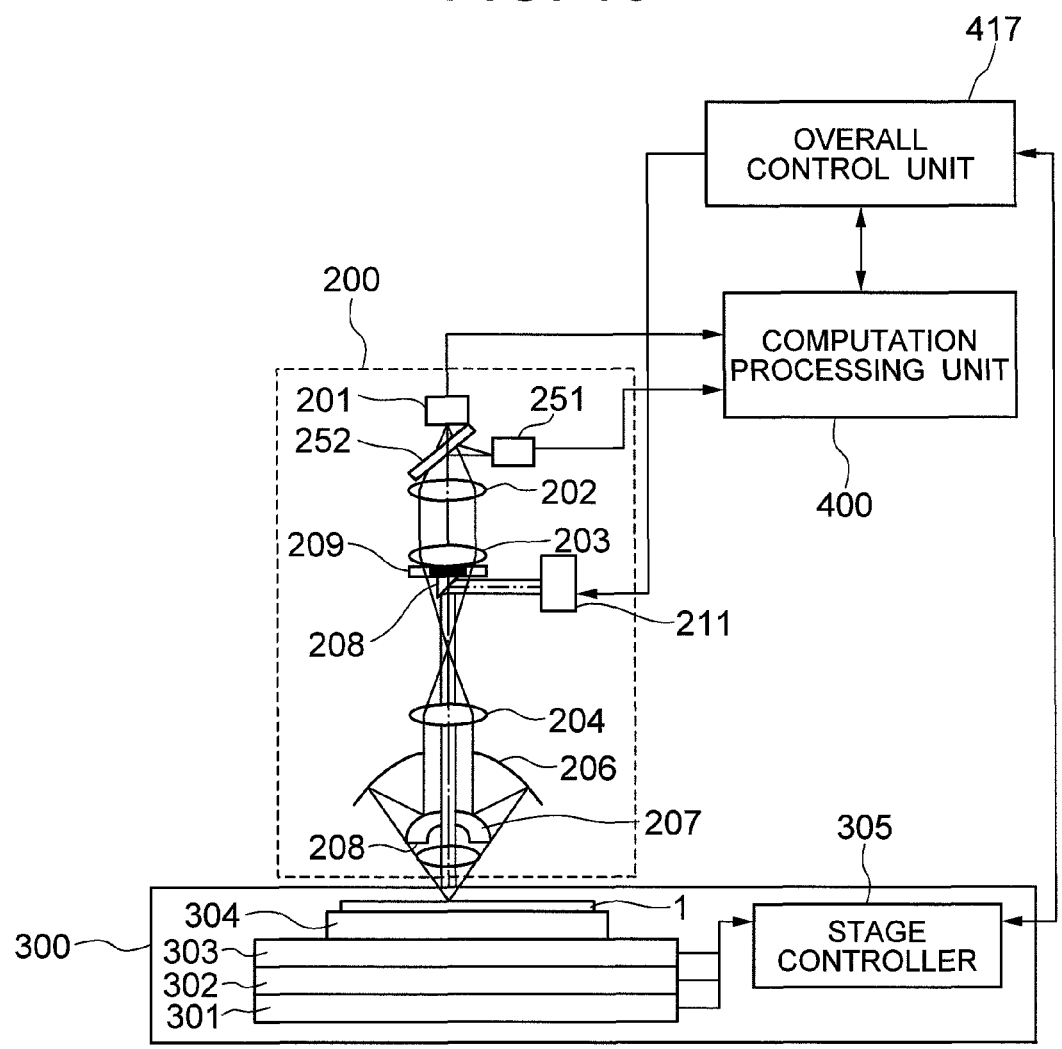
FIG. 18 shows a modified example of the defect inspection device according to the invention.

The invention claimed is:

1. A defect inspection device comprising:
 a light source;
 a catadioptric objective lens configured to collect light reflected from a sample surface, said light originally emitted from said light source, and to transmit said collected light in a vertical direction in relation to the sample surface;
 an imaging lens configured to focus specularly reflected light of said reflected light transmitted through said catadioptric objective lens;
 a blocking member configured to block light, the blocking member being disposed at a position at which specularly reflected light of said reflected light is focused by said imaging lens;
 a relay lens configured to focus reflected light not blocked by said blocking member;
 a detector configured to detect reflected light focused by the relay lens; and
 a computation processing unit configured to detect defects of said sample, on the basis of reflected light detected by said detector.

2. A defect inspection device according to claim 1, wherein said catadioptric objective lens has a dioptric lens for refracting said reflected light, and a first reflecting surface for reflecting scattered light among said reflected light; and
 wherein said dioptric lens has a second reflecting surface for reflecting said scattered light reflected from said first reflecting surface.

3. A defect inspection device according to claim 1, wherein said blocking member is provided at another relay lens.

4. A defect inspection device according to claim 1, wherein said catadioptric objective lens includes: a dioptric lens for refracting said reflected light, a reflecting member having a first reflecting surface for reflecting scattered light among said reflected light, a region for reflecting said scattered light reflected by said first reflecting surface, and a region for transmitting said specularly reflected light.

5. A defect inspection device according to claim 1, wherein said blocking member is provided to a spatial filter interposed between said imaging lens and said relay lens.

6. A defect inspection device according to claim 3, wherein said blocking member includes a reflecting film applied to a surface of said another relay lens.

7. A defect inspection device according to claim 4, which has a half mirror for reflecting illumination light emitted from said light source and radiating the illumination light to said sample.

8. A defect inspection device according to claim 7, wherein said first reflecting surface is interposed between said half mirror and said sample.

9. A defect inspection device according to claim 5, wherein said blocking member includes a blocking film applied to said spatial filter.

10. A defect inspection device according to claim 5, wherein said blocking member includes a circular cylindrical member provided to said spatial filter.

11. A defect inspection device according to claim 10, wherein said circular cylindrical member has a surface that reflects illumination light from said light source.

12. A defect inspection device comprising:
 a light source;
 a catadioptric objective lens configured to collect light reflected from a sample surface, said light originally emitted from said light source, and to transmit said collected light in a vertical direction in relation to the sample surface;

an imaging lens configured to focus specularly reflected light of said reflected light transmitted through said catadioptric objective lens;

a first relay lens, including a blocking member configured to block light, the blocking member being disposed at a position on the first relay lens at which specularly reflected light of said reflected light is focused by said imaging lens;

a second relay lens configured to focus reflected light not blocked by said blocking member of said first relay lens, wherein said first relay lens is interposed between said imaging lens and said second relay lens;

a detector configured to detect reflected light focused by the second relay lens; and a computation processing unit configured to detect defects of said sample, on the basis of reflected light detected by said detector.

13. A defect inspection device according to claim 12, wherein said catadioptric objective lens includes: a dioptric lens for refracting said reflected light, a reflecting member having a first reflecting surface for reflecting scattered light among said reflected light, a region for reflecting said scattered light reflected by said first reflecting surface, and a region for transmitting said specularly reflected light.

14. A defect inspection device according to claim 12, wherein said catadioptric objective lens has a dioptric lens for refracting said reflected light, and a first reflecting surface for reflecting scattered light among said reflected light; and wherein said dioptric lens has a second reflecting surface for reflecting said scattered light reflected from said first reflecting surface.

15. A defect inspection device according to claim 13, which has a half mirror for reflecting illumination light emitted from said light source and radiating the illumination light to said sample.

16. A defect inspection device according to claim 15, wherein said first reflecting surface is interposed between said half mirror and said sample.

17. A defect inspection device comprising:

a light source;

a catadioptric objective lens configured to collect light reflected from a sample surface, said light originally emitted from said light source, and to transmit said collected light in a vertical direction in relation to the sample surface;

an imaging lens configured to focus specularly reflected light of said reflected light transmitted through said catadioptric objective lens;

a spatial filter, including a blocking member configured to block light, the blocking member being disposed at a position on the spatial filter at which specularly reflected light of said reflected light is focused by said imaging lens;

a relay lens configured to focus reflected light not blocked by said blocking member of said spatial filter, wherein said spatial filter is interposed between said imaging lens and said relay lens;

a detector configured to detect reflected light focused by the relay lens; and a computation processing unit configured to detect defects of said sample, on the basis of reflected light detected by said detector.

18. A defect inspection device according to claim 17, wherein said catadioptric objective lens includes: a dioptric lens for refracting said reflected light, a reflecting member having a first reflecting surface for reflecting scattered light among said reflected light, a region for reflecting said scattered light reflected by said first reflecting surface, and a region for transmitting said specularly reflected light.

19. A defect inspection device according to claim 17, wherein said catadioptric objective lens has a dioptric lens for refracting said reflected light, and a first reflecting surface for reflecting scattered light among said reflected light; and wherein said dioptric lens has a second reflecting surface for reflecting said scattered light reflected from said first reflecting surface.

20. A defect inspection device according to claim 18, which has a half mirror for reflecting illumination light emitted from said light source and radiating the illumination light to said sample.

21. A defect inspection device according to claim 20, wherein said first reflecting surface is interposed between said half mirror and said sample.

* * * * *